(12) United States Patent
Lin et al.

(10) Patent No.: US 7,253,177 B2
(45) Date of Patent: Aug. 7, 2007

(54) SYNTHESIS AND ANTIMALARIAL ACTIVITY OF PYRROLO[3,2-F]QUINAZOLINE-1,3-DIAMINE DERIVATIVES

(75) Inventors: Ai J. Lin, Potomac, MD (US); Jian Guan, Olney, MD (US); Quan Zhang, Rockville, MD (US); Donald R. Skillman, Silver Spring, MD (US)

(73) Assignee: United States of America as Represented by the Secretary of the Army, Washington, DC (US)

( * ) Notice: Subject to any disclaimer, the term of this patent is extended or adjusted under 35 U.S.C. 154(b) by 272 days.

(21) Appl. No.: 10/971,846

(22) Filed: Oct. 22, 2004

(65) Prior Publication Data

US 2006/0094736 A1    May 4, 2006

(51) Int. Cl.
| | |
|---|---|
| *A01N 43/54* | (2006.01) |
| *A61K 31/505* | (2006.01) |
| *C07D 239/00* | (2006.01) |
| *C07D 471/00* | (2006.01) |
| *C07D 487/00* | (2006.01) |
| *C07D 491/00* | (2006.01) |

(52) U.S. Cl. ...................................... 514/267; 544/247
(58) Field of Classification Search ................ 544/247; 514/267
See application file for complete search history.

(56) References Cited

U.S. PATENT DOCUMENTS 4,118,561 A * 10/1978 Ledig .......................... 544/250
4,208,520 A    6/1980 Ledig et al.

FOREIGN PATENT DOCUMENTS

WO   WO/02/068425 A   9/2002

OTHER PUBLICATIONS

Ho-Sam Ahn, et al., Structure-Activity Relationships of Pyrroloquinazolines as Thrombin Receptor Antagonists, Biooganic & Medicinal Chemistry Letters 9 (1999) 2073-2078.*

* cited by examiner

*Primary Examiner*—Zachary C. Tucker
*Assistant Examiner*—Erich A. Leeser
(74) *Attorney, Agent, or Firm*—Elizabeth Arwine

(57) ABSTRACT

The invention relates to derivatives of pyrroloquinazolinediamine, more specifically derivatives of 7-(substituted)-7H-pyrrolo[3,2-F] quinazoline-1,3-diamines that are non-toxic and are also effective in the treatment of malaria, including *P. falciparum* and *P. vivax* strains. The derivatives are certain carbamate derivatives, succinimide derivatives, alkylcarboxamides derivatives and acetamide derivative, phthalimides, alkylamines and all other amide and imide derivatives and their 1-hydroxy analogs. The derivatives of the present invention are also soluble in common organic solvents to facilitate the purification in a large scale synthesis of the composition.

66 Claims, 2 Drawing Sheets

SYNTHESIS AND ANTIMALARIAL ACTIVITY OF PYRROLO[3,2-F]QUINAZOLINE-1,3-DIAMINE DERIVATIVES

GOVERNMENT INTEREST

The invention described herein may be manufactured, used and licensed by or for the U.S. Government.

BACKGROUND OF THE INVENTION

1 Field of the Invention

The present invention relates to new compounds that are useful for the treatment of malaria. The compounds of the invention are pyrroloquinazolinediamine derivatives, namely alkyl derivatives, carbamate derivatives, succinimide derivatives, alkylcarboxamides derivatives, including acetamide, phthalimide, and all other amide and imide derivatives of the parent compound 1 and their analogs that are effective and less toxic for treatment of malaria, including but not limited to P. falciparum and P. vivax strains.

2 Brief Description of Related Art

The current global situation with respect to malaria indicates that about two billion people are exposed to the disease. Each year between 100 to 200 million new cases of infection are reported and approximately 1 to 2 million people die due to malaria [1, 2]. US ground troops suffered high percentage of casualties by malaria infection during the Vietnam War and recently among British and US soldiers deployed in Somalia, Africa [3]. The situation of malaria control is rapidly worsening mainly due to non-availability of effective drugs and development of drug resistance to the existing first line drugs [4, 5]. Furthermore, the usefulness of many newer antimalarial drugs was impaired by their side effects. Lethal hemolysis side effect was observed in glucose-6-phosphate dehydrogenase (G6PD) deficient recipients of 8-aminoquinoline drugs [6] (primaquine and tafenoquine) and CNS toxicity was problematic in the patients treated with mefloquine [7]. Therefore, there is an eminent need for new and safe antimalarial compounds to combat these parasites in the epidemic areas of the world.

Pyrroloquinazolinediamine derivatives were reported to possess anticancer, antimicrobial and antimalarial activities (See Ledig, et al. U.S. Pat. No. 4,118,561) [8]. Among the derivatives, WR227825 (1) is one of the most potent antimalarial agents ever reported [9]. This compound displayed not only high in vitro efficacy against P. falciparum with IC50~0.01 ng/ml but also highly active against P. berghei in rodent model, with 100% curative oral dose between <0.1 to 4 mg/kg. However, Ledig, et al. WR227825 also exhibited high host toxicity, with subcutaneous $LD_{50}$ in mice at less than 20 mg/kg and produced deaths in Aotus monkey at doses less than 2 mg/kg [10]. The low therapeutic index of compound 1 has severely limited its value as an antimalarial agent. Nevertheless, the high efficacy and low therapeutic index of Ledig, et al., WR227825 make this compound an ideal lead for optimization to fabricate new derivatives with improvement in therapeutic index or deficiencies in preclinical/pharmacological profiles.

In addition to high host toxicity, the lead compound 1 is sparingly soluble in common organic solvents and water, a highly undesirable physical property for large scale synthesis and purification.

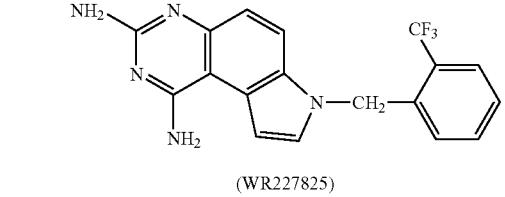

(WR227825)

What is needed is a composition that is effective against both drug sensitive and multi-drug resistant strains of malaria, especially P. falciparum and P. vivax and is substantially less toxic than WR 227825 so that it can be used safely in humans. What is also needed is a composition that is soluble in common organic solvents to facilitate the purification in a large scale synthesis of the composition. The parent compound 1 is sparingly soluble in either water or common organic solvents, which is a challenging problem to overcome during its large scale preparation.

The present invention solves the toxicity problems of the prior art by providing novel derivatives of WR227825 that have been found by the inventors to be substantially less toxic and more soluble in organic solvents than WR227825.

SUMMARY OF THE INVENTION

The present invention is directed to derivatives of:

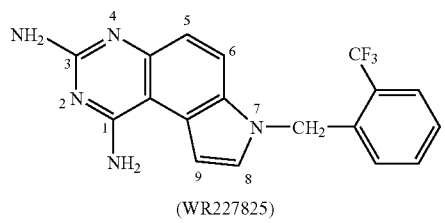

(WR227825)

wherein the amino groups at 1 and 3 positions have been substituted to render the compound a carbamate derivative, succinimide derivative, alkyl derivatives and alkylcarboxamide derivative including acetamide, phthalimide, or all other amide and imide derivatives. The compound 1 has been further modified by replacing one of the amino groups at 1-position with a hydroxy function.

DETAILED DESCRIPTION

Figure 1:
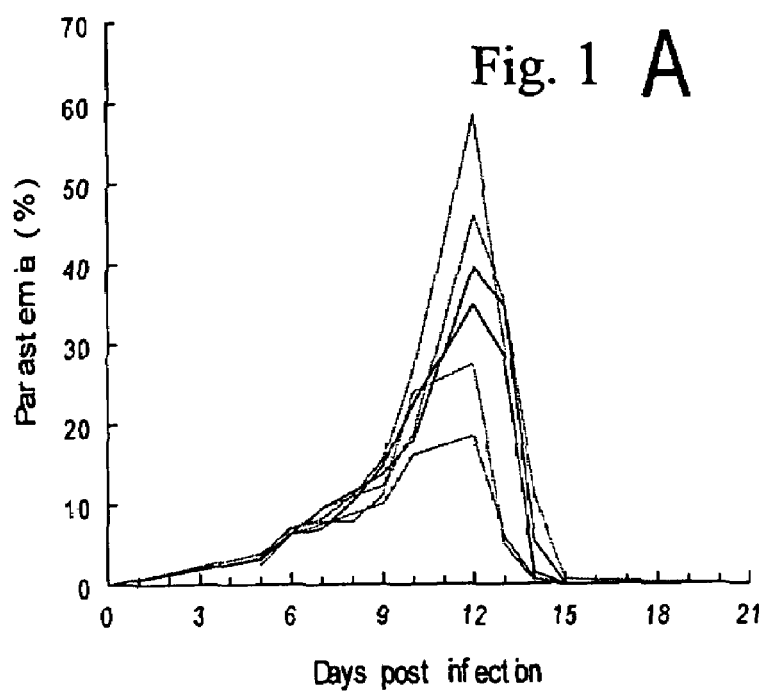
FIGS. 1A-D are graphs showing parasitemia responses in individual rat infected with P. berghe ANKA: (A) vehicle control with 1% CMC suspension; (B) 5 mg/kg of WR288901 (3e) with 100% curative measurement; (C) 10 mg/kg of WR288901(3e) with 100% curative effect, and (D) 20 mg/kg of WR288901 (3e) with 100% curative measurement in all animals following daily intragastric administration for three days (at day 6, 7, and 8 post-inoculation) treatments (n=2-5).
Figure 1:
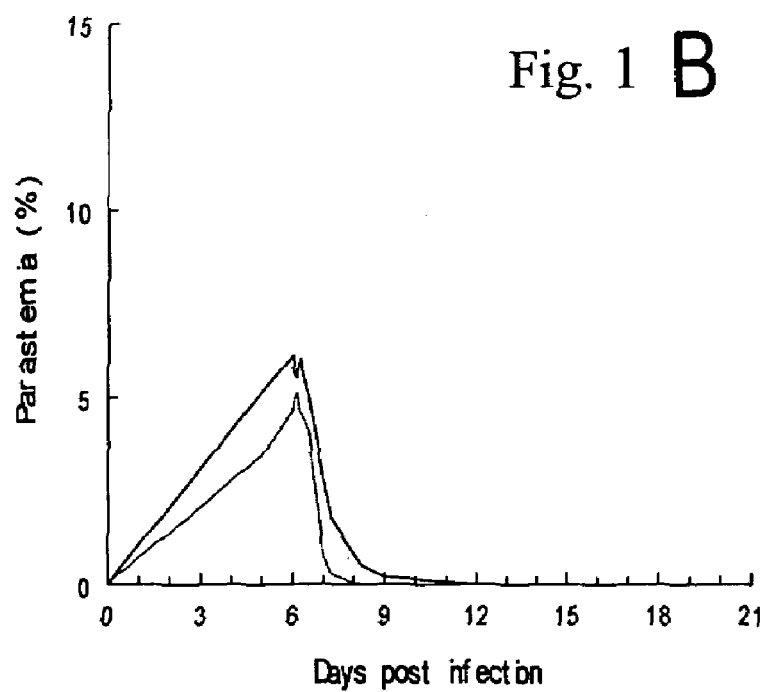
Figure 1:
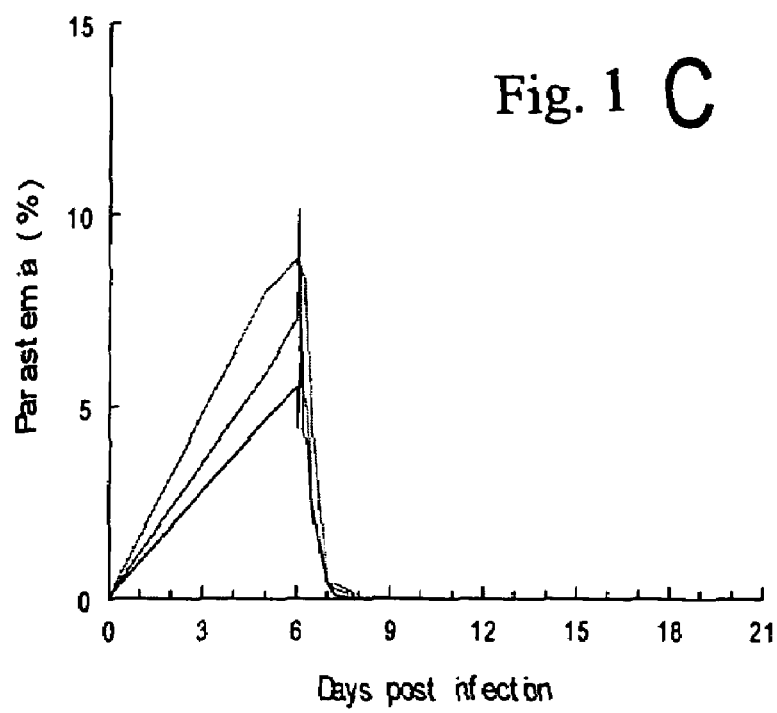
Figure 1:
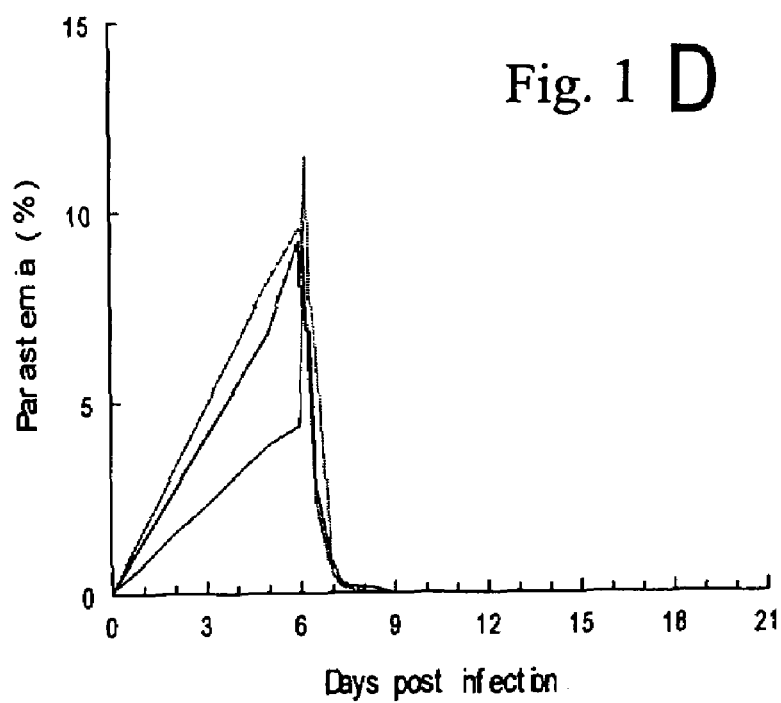

In this invention, we have initially synthesized a series of alkylcarbamates of WR227825 (2a-m) as shown in Table 1. All of the carbamates prepared, except 2-chlorobenzylcarbamate 2m, showed low in vitro activities against D-6, RCS, W-2 and TM91C235 clones of Plasmodium falciparum (Table 3), yet retained high in vivo activities against P. berghei (Table 4-5) in mouse, suggesting that carbamates of WR227825 may act as prodrugs which generate parent compound 1 in vivo. However, the carbamates all showed much higher tolerance (less toxic) than the parent molecule in the mice tests. Further, we explored the potential of carboxamides as a way to improve the therapeutic index by synthesizing a series of alkylcarboxamides and succinimides of WR227825 (Table 2) (3a-g), with which the amino groups, essential for DHFR inhibition, were tied down with acyl functions. Contrary to the existing knowledge of structure activity relation of antifolates which the free amino groups are essential for inhibitory activity, and the reported stability of amides and succinimides, the new acetamides and imides are not only highly active in in vitro tests against D-6, RCS, W-2 and TM91C235 clones of P. falciparum ($IC_{50}$ ~0.01 ng/mL) (Table 3), but also highly potent in the rodent Thompson test against P. berghei in mouse (100% cure at oral dose from <1 mg/kg to 220 mg/kg) [Tables 4 and 5]. Since amides are generally stable chemically and enzymatically in vivo, the high in vitro and in vivo efficacy of amides 3a-g were unexpected, suggesting that the amides and succinimides possess intrinsic antimalarial activity.

completely prevented parasitemia formation at doses from 0.65 to 40 mg/kg given orally for 3 consecutive days [Table 6].

Testing against P. falciparum in Aotus monkey, both 2b and 3e cleared parasitemia by day 3 at oral dose of 1 mg/kg and no recrudescence was observed for >100 days. Against a clone of P. vivax which has four dihydrofolate reductase (DHFR) mutations and is highly resistant to antifolates, such as pyrimethamine and cycloguanil, 3e cured Aotus monkeys at both 1 and 3 mg/kg/day×3 po. Compound 2b was, however, less active at the same doses [Table 7]. Administered orally at 3 mg/kg, both compounds showed moderate presumptive causal prophylactic activity against P. cynomolgi in Rhesus monkeys, delaying the parasitemia development from 8 days for untreated control to 18-23 days of the treated monkeys after challenged with sporozoites, a protection of 8-15 days. [see Experimental Section (h). Protocol and Results].

Compound 3e has shown a very high therapeutic index (>160) in rats. No host toxicity was seen at any dose in efficacy studies of 3e in all species of animal models studied. In mice, no drug-related deaths were observed with oral dosing of 3e up to 220 mg/kg×3 in mice and up to 800 mg in rats by a single oral dose [Table 8]. In Aotus monkeys, no behavior, weight or blood chemistry changes were observed

TABLE 1

Pyrroloquinazolinediamine Carbamates

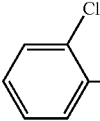

| | $R_1$ | $R_2$ | $R_3$ | $R_4$ |
|---|---|---|---|---|
| 2a | H | H | $CH_3CH_2OC=O$ | H |
| a' | $CH_3CH_2OC=O$ | H | H | H |
| b | $CH_3CH_2OC=O$ | H | $CH_3CH_2OC=O$ | H |
| c | $CH_3CH_2OC=O$ | H | $CH_3CH_2OC=O$ | $CH_3CH_2OC=O$ |
| d | $CH_3CH_2OC=O$ | $CH_3CH_2OC=O$ | $CH_3CH_2OC=O$ | $CH_3CH_2OC=O$ |
| e | $(CH_3)_2CHOC=O$ | H | $(CH_3)_2CHOC=O$ | H |
| f | $(CH_3)_2CHOC=O$ | H | $(CH_3)_2CHOC=O$ | $(CH_3)_2CHOC=O$ |
| g | H | H | $(CH_3)_3COC=O$ | H |
| h | H | H | $(CH_3)_3COC=O$ | $(CH_3)_3COC=O$ |
| i | H | $(CH_3)_3COC=O$ | $(CH_3)_3COC=O$ | $(CH_3)_3COC=O$ |
| j | $(CH_3)_3COC=O$ | $(CH_3)_3COC=O$ | $(CH_3)_3COC=O$ | $(CH_3)_3COC=O$ |
| k | H | H | $(CH_3)_2CHCH_2OC=O$ | H |
| l | $(CH_3)_2CHCH_2OC=O$ | H | $(CH_3)_2CHCH_2OC=O$ | H |
| m | H | H | 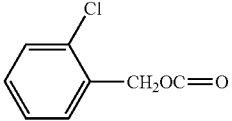 | (same 2-Cl-benzyl-$OC=O$ group) |

Among the compounds synthesized, two of the best derivatives (2b and 3e) with the best antimalaria activity against P. berghei in mice were further tested against P. berghei in rats, P. yoelii in mouse, P. cynomolgi in Rhesus monkey and P. falciparum and P. vivax in Aotus monkeys. Compound 3e produced 100% cure against P. berghei in rats at doses of 5, 10 and 20 mg/kg×3 administered orally [FIG. 1]. Against P. yoelii in sporozoite challenged mouse, 3e when treated with a single oral dose (3 mg/kg) of 2b and 3e [See Experimental Section (e) Toxicity Study in Aotus Monkey]. It was further noted that neither 2b nor 3e exhibited any sign of toxicity in P. cynomolgi-infected Rhesus monkeys receiving 12 mg/kg/day for 7 consecutive days.

Inhibition of dihydrofolate reductase (DHFR) was reported to be the mechanism of action of 1,3-diaminopyrroloquinazolines. [John J. McCormack, Barbara A. Allen, Kurt W. Ledig, and Brian L. Hillcoat, "Inhibition of Dihydrofolate Reductases by Derivatives of 2,4-diaminopyrroloquinazoline" Biochem. Pharmacol. (1979) 28, 3227-3229]. The cell growth inhibition by 1,3-diaminopyrroloquinazoline derivatives and the analogous diaminoquinazolines or triazines, however, was not reversed by addition of folinic acid in the cell culture, indicating that this class of compound may also inhibit other enzyme targets, other than dihydrofolate reductase. [Milhou, Wilbur K.; et al, Antimicrob. Agents ad Chemother. (9185), 27 (4), 525-30., Genther, Clara S. et al., J. Med. Chem. (1977), 20 (2), 237-43.] Since carboxamides and especially acetamides are chemically and enzymatically stable and 1,3-diamino groups of 1 are essential for inhibition of dihydrofolate reductase (DHFR) [Elslager, Edward F., et al, J. Med. Chem., (1979), 22 (10), 1247-57.; Rosowsky, Andre., et al., J. Med Chem., (1974), 17 (11), 1217-22.; Elslager, Edward F., et al, J. Med. Chem., (1972), 15 (8), 827-36., Davoll, John, et al., J. Med. Chem., (1972), 15 (8), 812-26], the extremely high antimalarial activity of acetamides (3a-e) in cell culture as well as in Thompson test was an unexpected and surprising discovery. Furthermore, the alkylcarbamates, acetamides and succinimide derivatives (2a-m and 3a-g) are all substantially less toxic than the parent compound 1.

TABLE 2

Pyrroloquinazolinediamine Carboxamides and Succinimides

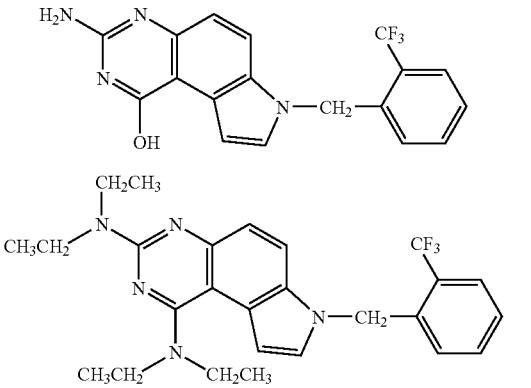

| | $R_1$ | $R_2$ | $R_3$ | $R_4$ |
|---|---|---|---|---|
| 3a | H | H | $CH_3C=O$ | H |
| b | H | H | $CH_3C=O$ | $CH_3C=O$ |
| c | $CH_3C=O$ | H | $CH_3C=O$ | H |
| d | $CH_3C=O$ | H | $CH_3C=O$ | $CH_3C=O$ |
| e | $CH_3C=O$ | $CH_3C=O$ | $CH_3C=O$ | $CH_3C=O$ |
| f | $R_1, R_2 = (CH_2C=O)_2$ | | H | H |
| g | $R_1, R_2 = (CH_2C=O)_2$ | | $R_3, R_4 = (CH_2C=O)_2$ | |

Although the oral lethal dose of the lead compound in Aotus monkey is at less than 2 mg/kg, no behavior, weight or blood chemistry changes in Aotus monkeys was observed with a single oral dose of bis-ethylcarbamate (2b) and tetra-acetamide (3e) derivatives at 3 mg/kg [See Experimental Section (e) Toxicity Study in Aotus Monkey], a substantial improvement in therapeutic index over the parent compound. No high dose related death up to 80-220 mg/kg in mouse was observed among the carbamates or amides tested (Tables 4 and 5). Since amides and imides are chemically and enzymatically stable, most likely the parent molecules or their partially hydrolyzed products such as 3a-c and 3 f, possess potent intrinsic antimalarial efficacy and may not act simply as a prodrug of the lead compound 1.

Further structure activity relationship studies lead to the synthesis of 1-hydroxy-3-amino analog, compound 4, which showed 100% cure against *P. berghei* at oral dose range of 80-180 mg/kg (Table 5). Alkylation of 1 gave tetraethylamine (5) which is over ten thousand fold less active than the lead compound 1 against both sensitive and drug resistant *P. falciparum* cell lines in vitro (Table 3). However, compound 5 exhibited potent in vivo activity against *P. berghei* with curative oral dose of 10-80 mg/kg in Thompson test (Table 5). Compound 4 is an analog of compound 1 with 1-amino group being replaced with a hydroxy group. It is also possible to substitute $CF_3$ with F, Cl, Br, $CH_3$, $CF_3$ or $CH_3CH_2$ in compound 4. Compound 5 is an analog of compound 3e with the acetyl groups being replaced with chemically stable ethyl substituents.

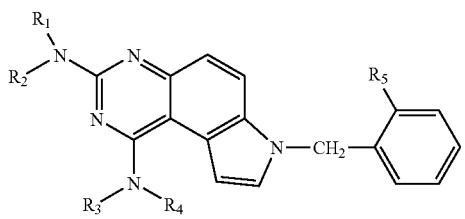

This invention covers the chemical syntheses and antimalarial activities of a series of $N^1,N^3$-mono-, bis-, tris- and tetra-alkyl, alkylcarbamates, alkylarylcarbamates, acetamides, phthalimides, succinimides, and all other amide and imide derivatives of the parent compound 1 and analogs with various substituents on 7-benzyl ring and hydroxy analogs of compound 4.

In another embodiment of the invention, an antimalarial of the Formula 6 and 7 are presented.

Formula 6

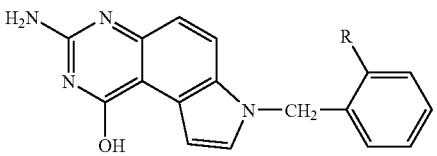

Where $R_1$, $R_2$, $R_3$, and $R_4$ are independently H, $CH_3C=O$, $(CH_2C=O)_2$,
$CH_3CH_2C=O$, $(CH_3)_2CHC=O$, $(CH_3)_3CC=O$,
$CH_3$, $CH_3CH_2$, $(CH_3)_2CH$, $(CH_3)_3C$, alkyl$C=O$,
or alkyl $R_5$ is independently F, Cl, Br, $CH_3$, $CF_3$, or $CH_3CH_2$ Formula 7

R=F, Cl, Br, $CH_3$, $CF_3$, or $CH_3CH_2$

It is to be understood that both the foregoing general description and the following detailed description are exemplary and explanatory only and are intended to provide further explanation of the invention as claimed.

Experimental Section

A. Chemistry:

Melting points were determined on a Mettler FP62 melting point apparatus and are uncorrected. Unless otherwise noted, all non-aqueous reactions were performed under an oxygen-free atmosphere of nitrogen with rigid exclusion of moisture from reagents and glassware. Analytical thin layer chromatography (TLC) was performed using HPTLC-HLF normal phase 150 microns silica gel plates (Analtech, Newark, Del.). Visualization of the developed chromatogram was performed by UV absorbance, or spreading with aqueous potassium permanganate, or ethanolic anisaldehyde. Liquid chromatography was performed using a Horizon HPFC System (Biotage, Charlottesville, Va.) with Flash 25M or 40M cartridges (KP-Sil™ Silica, 32-63 μm, 60 Å). Preparative TLC was performed using silica gel GF Tapered Uniplates (Analtech, Newark, Del.). Infrared spectra were recorded on a Bio-Rad FTS 3000 spectrophotometer (Bio-Rad Laboratories, Cambridge, Mass.) and are reported in reciprocal centimeters (cm$^{-1}$). $^1$H NMR and $^{13}$C NMR spectra were recorded in deuteriochloroform, unless otherwise noted, on a Bruker Avance 300 and Bruker Avance 600 spectrometer (Bruker Instruments, Inc, Wilmington, Del.). Chemical shifts are reported in parts per million on the δ scale from an internal standard of tetramethylsilane. Combustion analyses were performed by Atlantic Microlab, Inc. (Norcross, Ga.). Where analyses are indicated by symbols of the elements, the analytical results obtained were within +/−0.4% of the theoretical values.

The carbamates (2a-m) were prepared by a general procedure involving treatment of parent compound 1 with alkyl chloroformate or alkyl dicarbonate in chloroform under the catalysis of triethylamine and 4-dimethylaminopyridine. The product was purified by a silica gel column.

The acetamides (3a-e, Scheme 2) were prepared by the same method, except acetic anhydride instead of alkyl chloroformate or dicarbonate, was used as acylating agents. The reaction generally gave a mixture of the products as shown in scheme 2 when the molar ratio of compound 1 and acetic anhydride is less than 1:4. However, tetra-acetamide (3e) was the major product when the ratio was increased to 1:>8. When large excess of acetic anhydride (40 fold) was used, tetra-acetamide 3e was isolated in 65% yield.

1. Preparation of Carbamates of Compound 1:

Scheme 1:

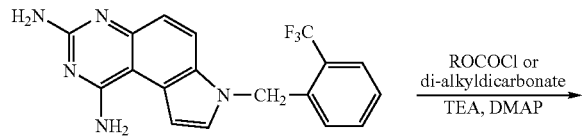

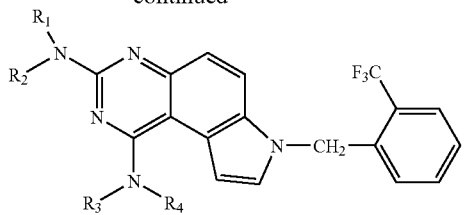

2

$R_1, R_2, R_3, R_4$ = ROC═O and/or H

General Procedure for Preparing Carbamates: To a mixture of compound 1 (5 g, 14 mmol) [Ledig, Kurt W., U.S. Pat. No. 4,118,561 (1978)], triethylamine (8.3 ml, 63 mmol), and DMAP (340 mg, 2.8 mmol) in 250 ml of CHCl$_3$, was added ethyl chloroformate (5.33 ml, 46 mmol) at 0° C. The reaction mixture was allowed to warm-up to room temperature and stirred overnight. The mixture was filtered with Celite. The filtrate was washed with H$_2$O and concentrated. The residue was applied on a silica gel column and eluted with 2% CH$_3$OH/CHCl$_3$ to yield 2b (2.4 g, 32%) and 2c (900 mg, 11%) which were recrystallized from CH$_3$OH/CHCl$_3$ to give pale yellow crystals a. Transformation of 2b to 2a and 2a':

(1). The suspension of 100 mg of 2b in ethyl acetate was refluxed for 2 h. The reaction mixture was evaporated to dryness and the residue was applied on a preparative TLC plate and developed with 5% CH$_3$OH/CHCl$_3$ to yield 2a, which was recrystallized from CH$_3$OH/CHCl$_3$ (60 mg, 50%).

(2). The suspension of 1 g of 2b in CH$_3$OH was added 1N HCl and refluxed overnight. The reaction mixture was neutralized with saturated NaHCO$_3$ and extracted with CHCl$_3$. The organic layer was washed with H$_2$O and dried. The residue was applied on a silica gel column and eluted with 3% CH$_3$OH/CHCl$_3$ to yield 600 mg of 2a'. Recrystallization of the crude from CH$_3$OH/CHCl$_3$ gave 425 mg (52%) of 2a' as colorless crystals.

The other derivatives were prepared according to the same general procedure, except t-Boc carbamate which t-Boc dicarbonate, instead of alkyl chloroformate, was used. The melting point, yield and NMR data are listed as follows:

2a: m.p. 187° C., 50%, $^1$H NMR (CDCl$_3$, 600 Hz) δ 7.78 (d, J=7.8 Hz, 1H), 7.60 (d, J=9.0, 1H), 7.54 (d, J=9.0, 1H), 7.41 (m, 2H), 7.36 (t, J=7.7 Hz, 1H), 6.90 (d, J=3.0 Hz, 1H), 6.51 (d, J=7.7 Hz, 1H), 6.02 (s, 2H), 5.71 (s, 2H), 4.31 (q, J=6.7 Hz, 2H), 1.35 (t, J=6.7 Hz, 3H). MS (m/z): 430 (M−), 384, 358. Anal. (C$_{21}$H$_{18}$N$_5$O$_2$F$_3$) C, H, N, F.

2a': m.p. 240° C., yield 52%, $^1$H NMR (CDCl$_3$, 300 Hz): δ 7.72 (d, J=7.2 Hz, 1H), 7.60 (d, J=3.0 Hz, 1H), 7.49 (d, J=9.0 Hz, 1H), 7.39 (d, J=3.0 Hz, 1H), 7.26-7.33 (m, 3H), 6.48 (d, J=7.4 Hz, 1H), 5.64 (s, 2H), 4.25 (q, J=7.2 Hz, 2H), 1.21 (t, J=7.2 Hz, 3H). MS (m/z): 431 (M+2). Anal. (C$_{21}$H$_{18}$N$_5$O$_2$F$_3$) C, H, N, F.

2b: m.p. 221° C., yield 32%, $^1$H NMR (CDCl$_3$, 300 Hz): δ 7.92 (d, J=2.8 Hz, 1H), 7.68 (d, J=7.5 Hz, 1H), 7.49 (d, J=8.7

Hz, 1H), 7.38 (d, J=2.8 Hz, 1H), 7.23-7.36 (m, 3H), 6.38 (d, J=7.5 Hz, 1H), 5.67 (s, 2H), 4.29-4.42 (m, 4H), 1.41 (t, J=6.9 Hz, 3H), 1.21 (t, J=7.2 Hz, 3H). MS (m/z): 502 (MH+). Anal. ($C_{24}H_{22}N_5O_4F_3$) C, H, N.

2c: m.p. 167° C., yield 11%, $^1$H NMR (CDCl$_3$, 300 Hz): δ 7.71-7.76 (m, 3H), 7.60 (s, 1H), 7.35-7.41 (m, 2H), 7.33 (d, J=3.0 Hz, 1H), 6.93 (d, J=3.0 Hz, 1H), 6.47 (d, J=7.5 Hz, 1H), 5.67 (s, 2H), 4.31 (q, J=7.2 Hz, 2H), 4.11-4.24 (m, 4H), 1.35 (t, J=7.2 Hz, 3H), 1.05 (t, J=7.2 Hz, 6H). MS (m/z): 574 (MH+). Anal. ($C_{27}H_{26}N_5O_6F_3$) C, H, N.

Isopropylcarbamates 2e and 2f were prepared according to the same procedure for the preparation of 2b, except isopropyl chloroformate was used as reagent.

2e: m.p. 225° C., yield 33%., $^1$H NMR (CDCl$_3$, 300 Hz): δ 8.01 (d, J=3.0 Hz, 1H), 7.71 (d, J=7.7 Hz, 1H), 7.52 (d, J=9.0 Hz, 1H), 7.38 (d, J=3.0 Hz, 1H), 7.22-7.36 (m, 3H), 6.37 (d, J=7.7 Hz, 1H), 5.67 (s, 2H), 5.06-5.27 (m, 2H), 1.39 (d, J=6.3 Hz, 6H), 1.16 (d, J=6.3 Hz, 6H). MS (m/z): 530 (MH+), 491, 444.

2f: m.p. 126° C., yield 4%, $^1$H NMR (CDCl$_3$, 300 Hz): δ 8.01 (d, J=3.0 Hz, 1H), 7.71 (d, J=7.7 Hz, 1H), 7.52 (1H, d), 7.38 (1H, d, J=3.0), 7.22-7.36 (3H, m), 6.37 (1H, d, J=7.7), 5.67 (2H, s), 5.06-5.27 (2H, m), 1.39 (6H, t), 1.16 (6H, t). MS (m/z): 615 (MH+), 530, 470, 444. Anal. ($C_{30}H_{32}N_5O_6F_3$) C, H, N.

t-Butylcarbamates 2 g-j were prepared according to the same procedure for the preparation of 2b, except t-Boc dicarbonate was used as reagent.

2g: m.p. 259° C., yield 27%, $^1$H NMR (CDCl$_3$, 600 Hz): δ 7.77 (d, J=7.7 Hz, 1H), 7.60 (d, J=9.0 Hz, 1H), 7.53 (d, J=9.0, 1H), 7.40 (m, 2H), 7.36 (t, J=7.2 Hz, 1H), 6.90 (d, J=3.6 Hz, 1H), 6.50 (d, J=7.7 Hz, 1H), 5.70 (s, 2H), 1.56 (s, 9H). MS (m/z): 458, 358. (MH+). Anal. ($C_{23}H_{22}N_5O_2F_3$) C, H, N.

2h: m.p. 280° C., yield 24%, $^1$H NMR (CDCl$_3$, 600 Hz): δ 7.76 (d, J=7.7 Hz, 1H), 7.62 (d, J=9.0 Hz, 1H), 7.41 (d, J=9.0 Hz, 1H), 7.39 (d, J=7.7 Hz, 1H), 7.34 (t, J=7.6 Hz, 1H), 7.30 (d, J=3.0 Hz, 1H), 6.96 (d, J=3.0 Hz, 1H), 6.48 d, J=7.7 Hz, 1H), 5.67 (s, 2H), 1.33 (s, 9H). MS (m/z): 558 (MH+), 384, 358; Anal. ($C_{28}H_{30}N_5O_4F_3$) C, H, N.

2i: m.p. 154° C., yield 13.6%, $^1$H NMR (CDCl$_3$, 600 Hz): δ 7.81 (d, J=9.1 Hz, 1H), 7.77 (d, J=7.8 Hz, 1H), 7.74 (d, J=9.1 Hz, 1H), 7.41 (t, J=7.5 Hz, 1H), 7.34 (m, 2H), 7.02 (d, J=3.0 Hz, 1H), 6.48 (d, J=7.8 Hz, 1H), 5.71 (s, 2H), 1.57 (s, 9H), 1.29 (s, 18H). MS (m/z): 658, 602, 358. (MH+). Anal. ($C_{33}H_{38}N_5O_6F_3·1/4CH_3CO_2C_2H_5$) C, H, N.

2j: m.p. 168° C., yield 20%, $^1$H NMR (CDCl$_3$, 600 Hz): δ 7.83 (s, 2H), 7.79 (d, J=7.8 Hz, 1H), 7.43 (d, J=7.5 Hz, 1H), 7.41 (d, J=3.0 Hz, 1H), 7.17 (d, J=3.0 Hz, 1H), 6.53 (d, J=7.8 Hz, 1H), 5.75 (s, 2H), 1.47 (s, 18H), 1.31 (s, 18H). MS (m/z): 758 (MH+), 584, 358. Anal. ($C_{38}H_{46}N_5O_8F_3·1/4H_2O$) C, H, N.

Isobutylcarbamates 2k and 2l were prepared from isobutyl chloroformate according to the general procedure for the preparation of ethylcarbamate 2b.

2k: m.p. 187° C., yield 52%, $^1$H NMR (CDCl$_3$, 600 Hz): δ 7.77 (d, J=7.7 Hz, 1H), 7.61 (d, J=9.0 Hz, 1H), 7.52 (d, J=9.0 Hz, 1H), 7.41 (m, 2H), 7.36 (t, J=7.5 Hz, 1H), 6.91 (d, J=3.0 Hz, 1H), 6.51 (d, J=7.7 Hz, 1H), 5.72 (s, 2H), 4.03 (d, J=6.7 Hz, 2H), 2.01(m, 1H), 0.99 (d, J=6.7 Hz, 6H). MS (m/z): 457 (MH+), 358. Anal. ($C_{23}H_{22}N_5O_2F_3$) C, H, N, F.

2l: m.p. 182° C., yield 6.4%, $^1$H NMR (CDCl$_3$, 300 Hz): δ 8.01 (d, J=3.0 Hz, 1H), 7.71 (d, J=7.7 Hz, 1H), 7.52 (1H, d), 7.38 (1H, d, J=3.0), 7.22-7.36 (3H, m), 6.37 (1H, d, J=7.7), 5.67 (2H, s), 5.06-5.27 (2H, m), 1.39 (6H, t), 1.16 (6H, t). MS (m/z): 558 (MH+), 458, 358.

Compound 2m was prepared using 2-chlorobenzyl chloroformate as reagent.

2m: m.p: 169° C., yield: 33%, $^1$H NMR (300 MHz, CDCl$_3$): δ, 7.75 (d, J=7.8 Hz, 1H), 7.63 (d, J=9.1 Hz, 1H), 7.44 (d, J=9.1 Hz, 1H), 7.38 (d, J=7.5 Hz, 1H), 7.32-7.03 (m, 10H), 6.71 (d, J =3.0 Hz, 1H), 6.45 (d, J=7.5 Hz, 1H), 5.62 (s, 2H), 5.31 (s, 4H), 5.27 (s, 2H); $^{13}$C-NMR: δ 158.77, 156.91, 153.39, 150.88, 135.55, 133.02, 132.61, 132.57, 131.48, 129.38, 129.28, 129.24, 129.17, 127.87, 127.15, 126.67, 126.08, 126.05, 120.54, 120.38, 119.96, 112.05, 102.98, 66.04, and 46.20; MS m/z: 694 (M+), 646.74, 606.07, 590.86, 550.75, 514.18, 448.14, 380.20, 358.15, 313.14, 287.20, 250.31, 237.05, 213.05, 185.07; Anal. ($C_{34}H_{24}Cl_2F_3N_5O_4$): C, H, N.

2. Preparation of Acetamides:

1,3-Bis(diacetylamino)-7-(2-trifluoromethyl)benzyl-7H-pyrrolo[3,2-f]quinazoline (3e): 7-[(2-Trifluoromethyl-phenyl)methyl]-7H-pyrrolo[3,2-f]quinazoline-1,3-diamine (1, 6.0 g, 16.8 mmol) was suspended in 300 ml of anhydrous chloroform. To the suspension was added dimethylaminopyridine (DMAP) (0.2 g, 1.6 mmol) and triethylamine (89 ml, 0.67 mol) at room temperature. The reaction mixture was cooled to 5° C. with an ice-bath and to the mixture, acetic anhydride (63.5 mL, 0.67 mol) was added dropwise. After the addition, the reaction mixture was stirred first at ice cold temperature for 30 mins, and then heated at 80° C. for 48 hrs. The solvent was removed by a rotary evaporator and the excess acetic anhydride was distilled under vacuum pump pressure. The crude solid was purified first by flush silica gel column chromatography using 1-5% ethyl acetate in chloroform as eluent to give a yellow solid. It was then further purified by recrystilization with EtOAc/Hexanes to yield the product as light yellow crystals (5.75 g, 65% yield). R$_f$=0.8; (EtOAc: CHCl$_3$, 1:1 v/v), mp 221° C.

From the reaction mixture, minor products (3d, 400 mg) and a small quantity of 3a, 3b, and 3c were isolated. The product ratio of 3a-d can be manipulated by changing the amount of acetic anhydride used, and the time and the temperature of the reaction.

The reaction generally gave a mixture of the products as shown in scheme 2 when the molar ratio of compound 1 and acetic anhydride is less than 1:4. However, tetra-acetamide (3e) was the major product when the ratio was increased to 1:>8. When large excess of acetic anhydride (40 fold) was used, tetra-acetamide 3e was isolated in 65% yield.

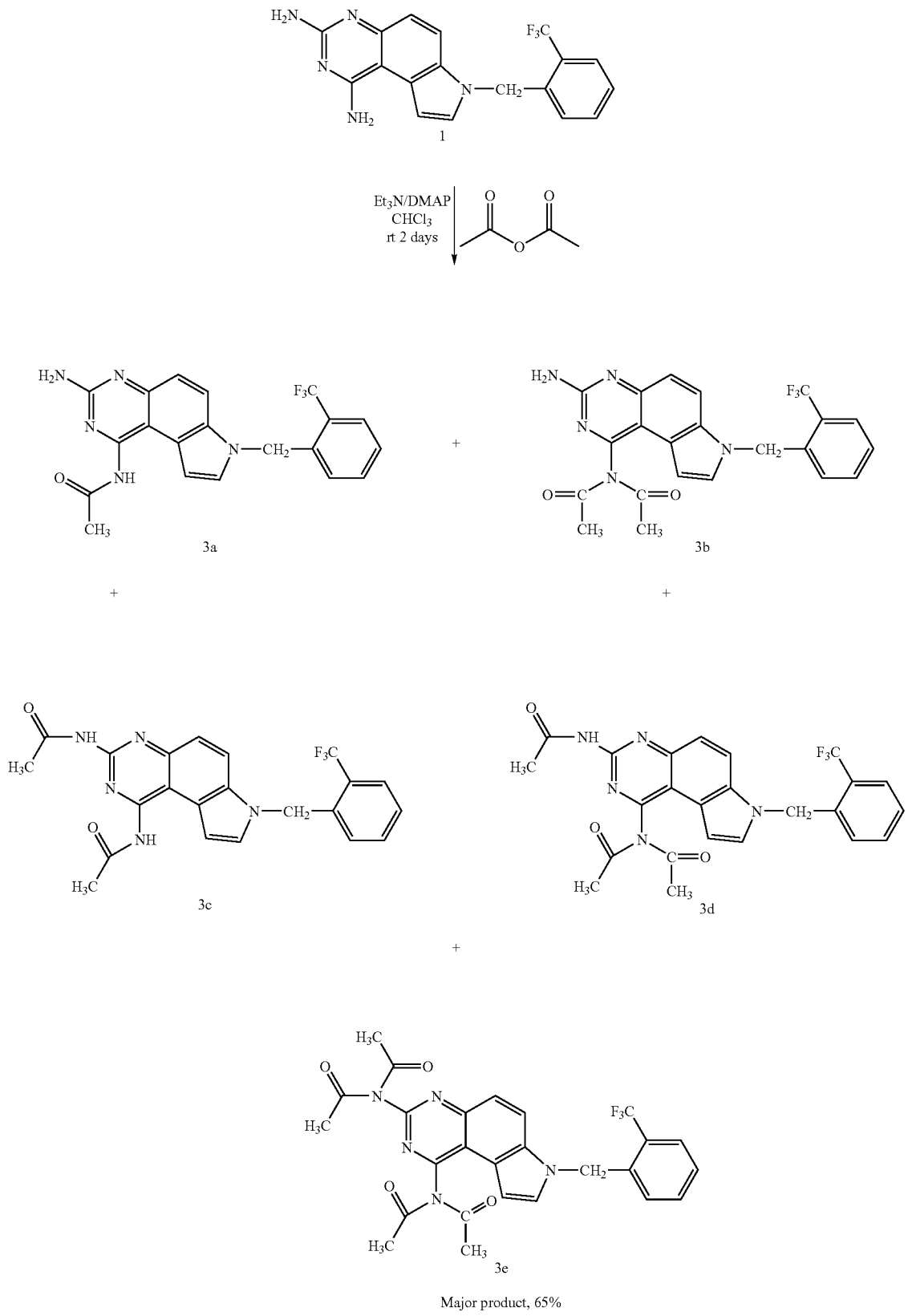

3a: mp 191° C.; $^1$H NMR (300 MHz, DMSO-d6) δ, 7.83-7.80(m, 1H), 7.67 (d, J=9.0 Hz, 1H), 7.57 (d, J=3.0 Hz, 1H), 7.49 (m, 2H), 7.18 (d, J=9.0 Hz, 1H), 6.83 (d, J=3.0 Hz, 1H), 6.42 (m, 1H), 5.76(s, 2H), 5.74 (s, 1H), 2.23 (s, 3H); MS m/z 400 (M$^+$+1), 359, 358, 287, 222, 167.

126.37, 122.69, 121.10, 119.43, 117.01, 47.19, 26.71, 26.47; IR: 1714, 1505, 1425, 1351, 1314, 1217, 1037,649, 579, and 559 cm$^{-1}$; MS m/z: 526 (M$^+$+1), 488, 442, 400, 359, 341, 289, 237; Anal. ($C_{26}H_{22}F_3N_5O_4$): C, H, N.

3. Preparation of Succinimides:

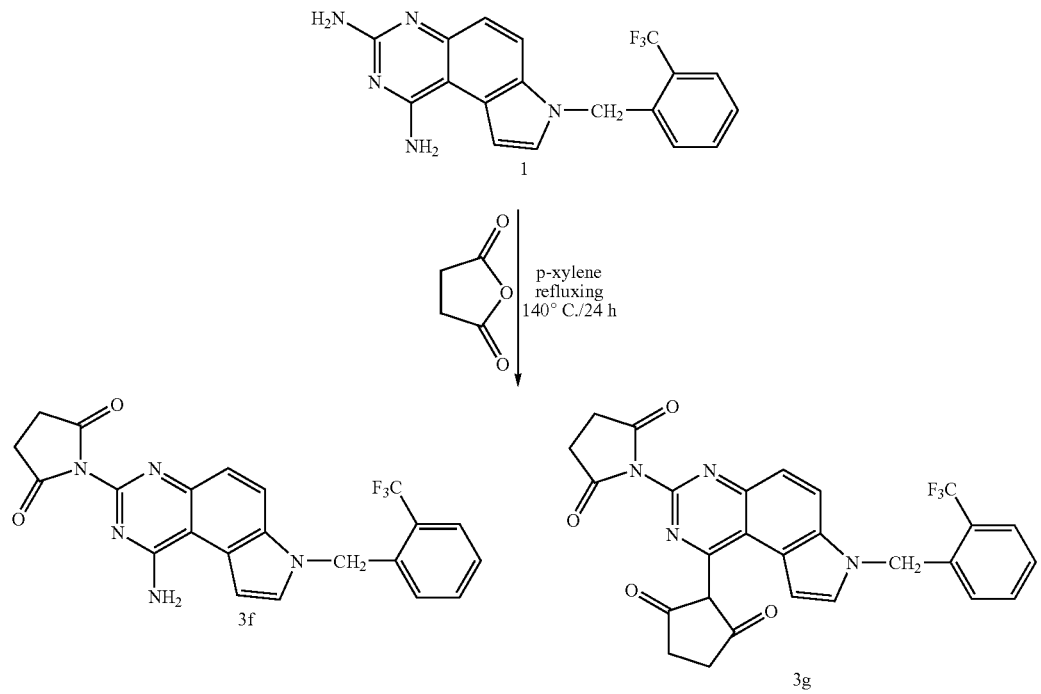

3b: Yellow solid, mp 229° C.; $^1$H NMR (300 MHz, CDCl$_3$): δ 7.82 (d, J=6.6 Hz, 1H), 7.78 (d, 1H, J=9.0 Hz, 1H), 7.61 (d, J=3.0 Hz, 1H), 7.51 (m, 2H), 7.28 (d, J=9.0 Hz, 1H), 6.55 (d, J=3.0 Hz, 1H), 6.49 (d, J=6.6 Hz, 1H), 5.76 (s, 2H), 2.41 (s, 6H); $^{13}$CNMR: δ 171.91,159.88, 159.10153.45, 135.36, 132.70, 131.69, 129.67, 127.94, 127.25, 126.20, 120.53, 120.44, 120.21, 112.34, 102.65, 47.70, 26.62; MS m/z: 441 (M$^+$), 400, 358, 316, 226, 199; Anal. ($C_{22}H_{18}F_3N_5O_2$): C, H, N.

3c: mp 210.6° C.; $^1$H NMR (300 MHz, CDCl$_3$): δ, 7.77 (d, J=7.5 Hz, 1H), 7.71 (d, J=9.1 Hz, 1H), 7.58 (d, J=9.1 Hz, 1H), 7.42 (d, J=3.0 Hz, 1H), 7.41-7.28 (m, 2H), 7.04 (d, J=3.0 Hz, 1H), 6.49 (d, J=7.5 Hz, 1H), 5.68 (s, 2H), 2.69 (s, 3H), 2.65 (s, 3H).

3d: mp 262° C., $^1$H NMR (300 MHz, DMSO): δ 8.05 (d, J=9.1 Hz, 1H), 7.84 (m, 1H), 7.75 (d, J=3.0 Hz, 1H), 7.66 (d, J=9.1 Hz, 1H), 7.55 (m, 2H), 6.80 (d, J=3.0 Hz, 1H), 6.54 (d, J=6.0 Hz, 1H), 2.31 (s, 6H), 2.22 (s, 3H); $^{13}$C-NMR: δ 172.01, 152.13, 133.73, 128.69, 127.88, 121.90, 121.23, 119.49, 114.34, 102.90, 26.68, 24.93; MS m/z: 484 (M$^+$+1), 464, 442, 400, 358, 323, 279, 219, 164.

3e: mp 221° C. $^1$H NMR (300 MHz, DMSO-d$^6$): δ 7.93 (d, J=9.2 Hz, 1H), 7.89 (d, J=9.2 Hz, 1H), 7.78 (d, J=7.2 Hz, 1H), 7.47 (d, J=3.1 Hz, 1H), 7.38 (m, 2H), 6.96 (d, J=3.1 Hz, 1H), 6.50 (d, J=7.2 Hz, 1H), 5.76 (s, 1H), 2.40 (s, 6H), 2.43 (s, 6H). $^{13}$C-NMR: δ 172.38, 171.84, 159.92, 153.27, 152.73, 134.71, 134.18, 132.81, 128.27, 127.14, 126.45, 1,3-Bis-(1-pyrrolidine-2,5-dione)-7-(2-trifluoromethyl)benzyl-7H-pyrrolo[3,2-f]quinazoline (3 g): 7-[(2-trifluoromethyl-phenyl)methyl]-7H-pyrrolo[3,2-f]-quinazoline-1,3-diamine (1) (0.25 g, 0.7 mmol) was suspended in 10 ml of anhydrous p-xylene. To the suspension was added dry molecular sieves (beads, 0.1 g), DMAP (20 mg) and succinic anhydride (0.56 g, 5.6 mmol) at room temp. After stirring for an hour at rt, triethylamine (0.4 ml, 2.8 mmol) was added. The reaction mixture was refluxed overnight, cooled down to room temperature and filtered to remove the molecular sieves. The filtrate was evaporated to dryness under reduced pressure. The solid residue was purified first with a flush silica gel column using 80% of ethyl acetate in chloroform as eluent to furnish an amorphous solid which was recrystalized from CHCl$_3$/acetone to give the bis-succinimide 3 g as light crystals (190 mg, 54%), mp>300° C. A small amount (5%) of 1-Amino-3-(1-pyrrolidine-2,5-dione)-7-(2-trifluoromethyl-benzyl)-7H-pyrrolo[3,2-f]quinazoline (3 f) was also isolated. The product ratio of 3 g and 3 f can be manipulated by changing the amount of succinic anhydride used in the reaction. The yield of 3 f increases as the molar ratio of succinic anhydride decreases.

3f: mp 284° C.; $^1$H NMR: (300 MHz, CDCl$_3$) δ, 7.76 (d, J=7.5 Hz, 1H), 7.69 (s, 2H), 7.47 (d, J=3.1 Hz, 1H), 7.32-7.38 (m, 2H), 6.95 (d, J=3.1 Hz, 1H), 6.38 (d, J=7.5 Hz, 1H), 5.74 (s, 2H), 2.94 (s, 4H); $^{13}$C-NMR: δ 175.62,162.93, 135.00, 133.55, 132.69, 130.43, 128.12, 127.07, 126.27, 121.38, 120.09, 118.63,106.97, 102.51, 47.10, 29.05; MS m/z: 440 (M⁺+1), 412, 393, 358, 341, 307, 279, 269, 247, 195, 181; IR (cm⁻¹): 1715, 1585, 1364, 1314, 1186, 1160, 1123, 840.

3g: $^1$H NMR (300 MHz, CDCl$_3$): δ, 7.90 (d, J=9.2 Hz, 1H), 7.86 (d, J=9.2 Hz, 1H), 7.75 (d, J=7.4 Hz, 1H), 7.41-7.32 (m, 3H), 6.66 (d, J=3.1 Hz, 1H), 6.35 (d, J=7.4 Hz, 1H), 5.73 (s, 2H), 3.16 (m, 4H), 2.99 (s, 4H); $^{13}$C-NMR: δ 176.63, 176.54, 154.20, 152.04, 148.00, 137.00, 134.24, 134.20, 134.00, 132.59, 128.67, 127.56, 126.00, 123.12, 121.57, 118.83, 104.24, 47.75, 29.99, and 29.38; MS m/z: 522 (M⁺+1), 440, 379, 342, 321, 257, 216, 197; IR (cm⁻¹): 1731, 1719, 1360, 1339, 1312, 1159, 1115, 762, 715; Anal. (C$_{22}$H$_{18}$F$_3$N$_5$O$_4$): C, H, N.

4. Preparation of Compound 4 and 5:

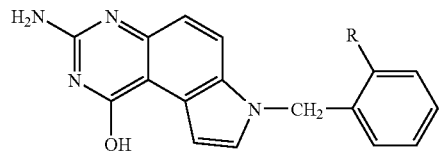

formula 4

Preparation of 1,3-bis-(diethylamino)-7-(2-trifluromethyl)benzyl-7H-pyrrolo[3,2-f]quinazoline (5): To a suspension of WR227825 (127 mg) in 5 ml of anhydrous THF, was added 45 mg of NaH in small portions at room temperature. The

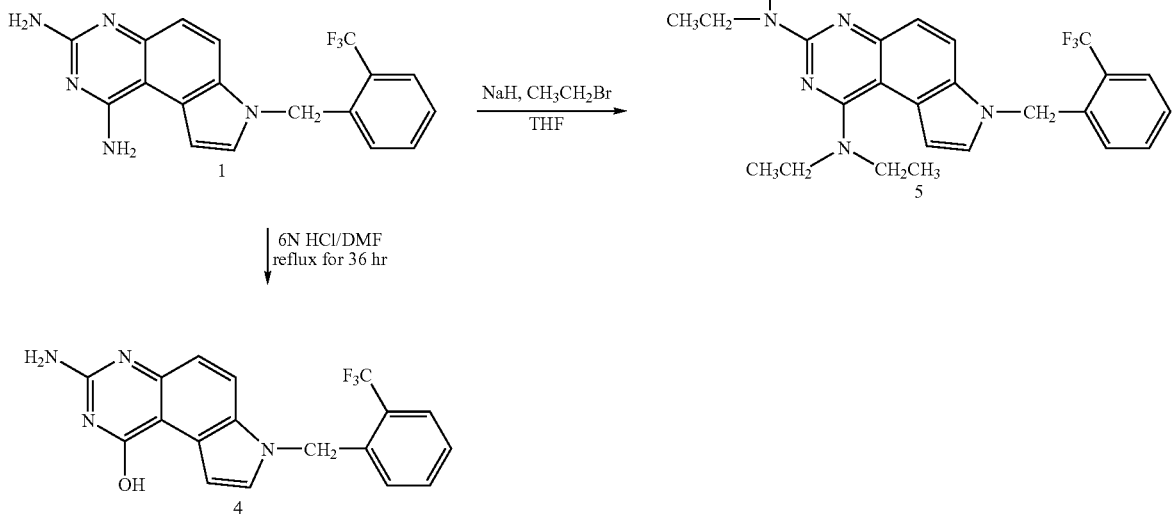

Scheme 4

Preparation of 1-hydroxy-3-amino-7-(2-trifluromethyl)benzyl-7H-pyrrolo [3,2-f]quinazoline (4): To the reaction mixture of 7-(2-trifluoromethyl)benzyl-7H-pyrrolo[3,2-f]-quinazoline-1,3-diamine (1,2.50 g, 7.00 mmol) in 3 ml DMF was added 200 ml of 6 N hydrochloric acid at room temperature. The aqueous solution was refluxed for 36 hrs. The solution was chilled and the pH of the solution was adjusted to pH 7 with 1N NaOH solution. The tan color precipitate was collected, washed with water and dried at 50° C. in vacuo. The crude product was purified by flush silica gel column chromatography using 0-10% methanol in CHCl$_3$ as eluent to furnish the title compound 4 as a white solid (1.132 g, 45% yield), mp >300° C. $^1$H NMR (300 MHz, DMSO): δ, 7.82-7.79 (m, 1H), 7.53 (d, J=3.0 Hz, 1H), 7.51-7.48 (m, 3H), 7.23 (m, 1H), 7.00 (d, J=8.8 Hz, 1H), 6.44 (m, 1H), 5.69 (s, 2H); $^{13}$C-NMR: δ 151.44, 137.15, 133.97, 131.67, 130.92, 128.40, 127.74, 126.71, 126.60, 126.52, 126.45, 126.38, 125.97, 125.19, 123.08, 117.46, 108.83, 103.31; MS m/z: 359 (M⁺+1), 342.20, 319.20, 299.27, 200.13, 159.13; Anal. (C$_{18}$H$_{13}$F$_3$N$_4$O0.5H$_2$O): C, H, N.

reaction mixture was stirred for 0.5 hr, followed by addition of 0.1 ml of ethyl bromide. The resulting reaction mixture was stirred at room temperature overnight and then quenched carefully with H$_2$O. The solution was extracted with ethyl acetate, dried and concentrated in vacuo. The residue was applied to a preparative TLC and eluted with 5% CH$_3$OH/CHCl$_3$ to yield compound 5 (63 mg, 40%), m.p. 237° C. (decomposed). $^1$H NMR (CDCl$_3$, 300 Hz): δ 7.72 (d, J=7.3 Hz, 1H), 7.28-7.42 (m, 4H), 7.19 (d, J=3.0 Hz, 1H), 7.03 (d, J=3.0 Hz, 1H), 6.45 (d, J=7.4 Hz, 1H), 5.66 (s, 2H), 3.73 (q, J=7.0 Hz, 4H), 3.61 (q, J=7.0 Hz, 4H), 1.24 (t, J=7.0 Hz, 6H), 1.55 (t, J=7.0 Hz, 6H). MS (m/z): 470 (MH+). Anal. (C$_{26}$H$_{30}$N$_5$F$_3$) C, H, N.

formula 5

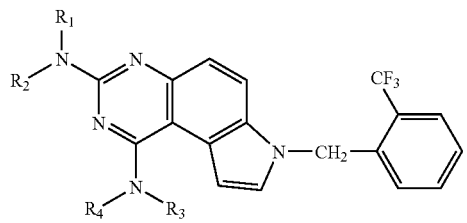

wherein $R_1$, $R_2$, $R_3$, and $R_4$ are independently H, $CH_3CH_2$, $(CH_3)_2CH$, $(CH_3)_3C$, or alky. $CF_3$ may also be replaced by $CH_3$, $CH_3CH_2$, Cl, Br, or F.

5. The invention also may encompass the preparation of compound of the formula 6 as follows:

Formula 6

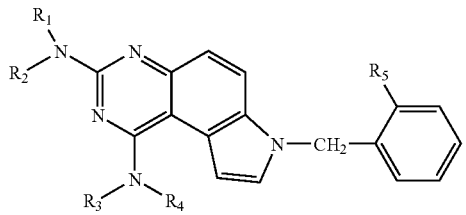

Where $R_1$, $R_2$, $R_3$, and $R_4$ are independently H, $CH_3C\!\!=\!\!O$, $(CH_2C\!\!=\!\!O)_2$, 
$CH_3CH_2C\!\!=\!\!O$, $(CH_3)_2CHC\!\!=\!\!O$, $(CH_3)_3CC\!\!=\!\!O$, 
$CH_3$, $CH_3CH_2$, $(CH_3)_2CH$, $(CH_3)_3C$, alkyl$C\!\!=\!\!O$, 
or alkyl $R_5$ is independently F, Cl, Br, $CH_3$, $CF_3$, or $CH_3CH_2$ Compounds of Formula 6 can be prepared from the starting material where $R_1$, $R_2$, $R_3$, $R_4$=H and $R_5$=F, Cl, Br, $CH_3$, or $CH_3CH_2$ following the same method for the preparation of 2a-m, 3a-g and 5 (where $R_5$=$CF_3$) as described above. The reaction is the same. Likewise, compounds with Formula 7 can be prepared according to the same method described for the synthesis of compound 4 using the same starting material for the preparation of compounds with Formula 6, where $R_1$, $R_2$, $R_3$, $R_4$=H and $R_5$=F, Cl, Br, $CH_3$, or $CH_3CH_2$. The reaction is the same.

Formula 7

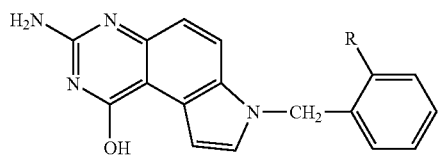

B. Antimalarial Activities:

(a). In Vitro Antimalarial Studies. The in vitro assays were conducted by using a modification of the semiautomated microdilution technique of Desjardins et al [11] and Chulay et al. [12]. Four P. falciparum malaria parasite clones, from CDC Indochina III (W-2), CDC Sierra Leone I (D-6), Southeast Asia Isolates (TM91C235) and RCS (Isolates from Brazil) were utilized in susceptibility testing. They were derived by direct visualization and micromanipulation from patient isolates [13]. The W-2 clone is susceptible to mefloquine but resistant to chloroquine, sulfadoxine, pyrimethamine, and quinine, whereas the D-6 clone is naturally resistant to mefloquine but susceptible to chloroquine, sulfadoxine, pyrimethamine and quinine. Test compounds were initially dissolved in DMSO and diluted 400 fold in RPMI 1640 culture medium supplemented with 25 mM Hepes, 32 mM $NaHCO_3$ and 10% Albumax I (Gibco BRL, Grand Island, N.Y.). These solutions were subsequently serially diluted two-fold with a Biomek 1000 (Beckman, Fullerton, Calif.) over 11 different concentrations. The parasites were exposed to serial dilutions of each compound for 48 hrs and incubated at 37° C. with 5% $O_2$, 5% $CO_2$ and 90% $N_2$ prior to the addition of [$^3$H]hypoxanthine. After a further incubation of 18 hrs, parasite DNA was harvested from each microtiter well using Packard Filtermate 196 Harvester (Meriden, Conn.) onto glass filters. Uptake of [$^3$H]hypoxanthine was measured with a Packard Topcount Scintillation. Concentration-response data were analyzed by a non-linear regression logistic dose response model and the $IC_{50}$ values (50% inhibitory concentrations) for each compound were calculated. (Table 3).

(b). In Vivo Antimalarial Studies against P. berghei in mice: The in vivo efficacy of the artelinic acid analogs were determined in a modified Thompson test. This test measures the survivability of mice and parasitemia clearance following administration of drug on days 3-5 post infection. In brief, $5\times10^6$ P. berghei-infected erythrocytes (KBG-173 strain) were inoculated intraperitoneally to female mice that weighed 24-30 g. By day three post-infection, parasitemia ranged from 1.0-3.7%. Each drug, dissolved in 5% sodium bicarbonate, was administered PO twice daily from day 3-5 post-infection. Total doses for each drug ranged from 1.5-384 mg/kg with 8 mice included in each dosage group. The percent suppression of parasitemia in the treated mice compared to the untreated controls was determined for each test compound; the SD-50 (fifty percent suppression dose) and SD-90 were determined from a non-linear regression logistic dose response fit at day 6 parasitemia data. Survival of mice to day 60 post-infection was considered a cure (C). Compounds were considered active (A) when the survival time of the treated mice was greater than twice the control mice, i.e., 12-14 day (Table 4-5).

(c). Sporozoite Induced Test

Each compound is ground with a mortar & pestle and suspended in 0.5% hydroxyethylcellulose—0.1% Tween 80 for compounds to be administered PO and those given SC are suspended in peanut oil. Each compound is prepared at 3 different dose levels as requested by WRAIR. Compounds are administered either PO or SC to mice once 4 hr before inoculation of sporozoites.

Four-week-old male CD-1 mice, purchased from Charles River and weighing 16-17 g, are placed 5 per cage and allowed to acclimate for 4 days before being treated and then inoculated with sporozoites. They are fed food and water ad-lib and maintained at 76° F. with 12 hr light and 12 hr darkness. The cages and water bottles are changed biweekly. The mice are weighed on Days 0, 3 and 6 then biweekly when blood films are taken.

*Plasmodium yoelii* (17×) is used to infect mice that will be used to infect the mosquitoes.

Mice are given a single dose of test compound 4 hr before being inoculated intraperitoneally with $2.5\times10^5$ sporozoites of *Plasmodium yoelii* on Day 0. Whole body weights are taken on Day 0 and Day 6 then twice a week for 31 days. A blood film is taken on Day 5 and then twice a week for 31 days. Mice loosing >20% of their body weight will be sacrificed. All mice alive on Day 31 with no parasites in a blood film at this time are considered cured. Donor mice used to infect the mosquitoes are infected with $2.5\times10^4$ parasitized erythrocytes. The mosquitoes are allowed to feed on these malaria-infected mice on Day 4 of their infection when the parasitemia is low.

i. Compound will be considered active against either the sporozoite or the EE stage if no parasites are found in the blood films taken on Day 5 or on subsequent blood films taken weekly for 31 days.

ii. A compound will be considered to exhibit marginal activity if only low levels of parasites are found (<10%) in blood films taken on Day 5 or any biweekly for 31 days.

iii. Mice alive on Day 31 with no parasites found in any blood films will be considered cured.

Results:

Compound 3e cured 100% of mice in dose groups from 0.625 to 40 mg/kg.

(d). In Vivo Antimalarial Studies against *P. berghei* in rats: All animals were quarantined for at least 7 days prior to infection. Rats were individually housed with food and water supplied ad libitum. Rats were then inoculated i.p. with cryopreserved *P. berghei*-infected rat blood ($2 \times 10^7$/rat in 0.5 ml Q.C. solution), obtained from donor rats infected one week earlier with cryopreserved parasites. Two pretreatment smears were taken from all animals for parasitemia analysis. Animals with >5% parasitemia were selected for the efficacy and tolerant dose studies. Eighteen post-treatment smears were obtained from each rat at 0, 3, 5, 8, and 12 hours on day 6, and at 0, 3, and 6 hours on day 7 and 8. From day 9 until day 21, blood smears were obtained from each animal once daily.

The nine groups of rats received test compounds at various doses of 0 (blank and vehicle controls), 1. 2, 5, 10, and 20 mg/kg intragastric administration once daily for 3 days. The dosing days were on days 6, 7, and 8, after the parasite inoculation day—day 0. Parasitemia suppression, clearance, and curative effects were measured during the studies. Clearance was deemed to have occurred if parasites were undetectable on two consecutive thin smears taken 24 h apart prior to day 12 (parasitemia continue to increase through this time in control rats). The 100% clearance and curative doses ($CD_{100}$) was defined as the lowest dose achieving 100% clearance in all animals without any toxicity. Experiment was terminated on day 21 (this is the time by which all surviving control animals would have cleared their infections).

During the efficacy studies, a maximum tolerant dose (MTD) was evaluated when the lethal dose was found following multiple treatments. In the MTD group, all animals were survived with no death up to 21 days of clinical observations. The results were shown on FIG. 1.

TABLE 3

Antimalarial Activity Against Plasmodium falciparum Cell Lines
($IC_{50}$ = ng/mL)

| Compound # | D-6[a] | W-2[b] | RCS[c] | TM91C235[d] |
|---|---|---|---|---|
| 1 | 0.0191 | 0.4453 | 0.3569 | 1.2178 |
| 2a | 20.709 | >250 | >250 | >250 |
| 2b | 7.9727 | 127.80 | >250 | >250 |
| 2c | >250 | >250 | >250 | >250 |
| 2h | 0.2549 | 3.6678 | 5.2370 | 26.366 |
| 2i | 1.9252 | 33.569 | 26.380 | 97.708 |
| 2n | 51.3815 | 75.7608 | 38.4855 | 74.1466 |
| 2p | 0.1269 | 0.2621 | | 0.4134 |
| 3a | 0.0097 | 0.0186 | 0.0096 | 0.0206 |
| 3b | 0.0101 | 0.0183 | 0.0116 | 0.0212 |
| 3e | 0.0236 | 0.0752 | 0.0236 | 0.0845 |
| 3g | 0.1284 | 0.1284 | 0.2571 | 0.4021 |
| 3f | <0.4883 | <0.4883 | | |
| 4 | 7.2403 | 53.9027 | | 83.3969 |
| 5 | 46.033 | 104.0182 | | |

[a]CDC Sierra Leone I (D-6),
[b]CDC Indochina III (W-2),
[c]RCS (Isolates from Brazil),
[d]TM91C235 (Southeast Asia Isolates).

TABLE 4

Antimalarial Activity against *Plasmodium berghei* by Subcutaneous Injection:

| Compound # | mg/kg/day | # Mice Dead/ Day Died | # Mice Alive Day 31/Total |
|---|---|---|---|
| Control | none | 2/8 1/9 3/10 | 0/6 |
| 1 | 40 | 1/6 1/8 2/9 3/10 | 0/7 |
| | 20 | 1/12 1/13 | 5/7 |
| | 10-2.5 | none | 7/7 |
| 2a | 40 | 2/17 | 5/7 |
| | 20-2.5 | none | 7/7 |
| 2h | 40-2.5 | none | 7/7 |
| 2i | 40-2.5 | none | 7/7 |
| 2j | 40 | 2/19 | 5/7 |
| | 20 | none | 7/7 |
| | 10 | 1/24 | 6/7 |
| | 2.5 | 1/10 1/11 2/20 1/24 | 2/7 |

TABLE 5

Oral Efficacy against *Plasmodium berghei*

| Compound # | Dose (mg/kg/day) | # Mice Dead/ Day Died | # Mice Alive Day 30/Total |
|---|---|---|---|
| 1 | 40 | 1/17 | 4/5 |
| | 20-1.25 | none | 5/5 |
| 2a | 40-2.5 | Death in each dose | 1/5-4/5 |
| 2b | 80-2.5 | None | 5/5 |
| | 1.25 | 1/24 1/27 | 3/5 |
| 2c | 80-1.25 | None | 5/5 |
| 2h | 80-2.5 | None | 5/5 |
| | 1.25 | 2/13 1/19 | 2/5 |
| 2p | 320-10 | None | 5/5 |
| 3d | 220-40 | None | 5/5 |
| | 10-0.625 | death in each group | 3/5 4/5 |
| 3e | 220-0.625 | None | 5/5 |
| 3g | 80 | 2/8 1/9 | 2/5 |
| | 40-10 | deaths in each group | 0/5 |
| 4 | 320 | 3/16 1/17 | 1/5 |
| | 160-80 | none | 5/5 |
| | 40-10 | deaths in each group | 1/5-2/5 |
| 5 | 160 | 1/11 1/12 1/13 1/14 | 4/8 |
| | 80-10 | none | 8/8 |

TABLE 6

Antimalarial Activity of 3e Against *P. yoelii*.

| Drug | Mg/kg | Route | Number of Mice Cured |
|---|---|---|---|
| 3e | 40 | oral | 5/5 |
|  | 10 |  | 5/5 |
|  | 2.5 |  | 5/5 |
|  | 0.625 |  | 5/5 |
|  | 0.3125 |  | 4/5 |
|  | 0.15625 |  | 4/5 |
| Tefenoquine | 10 | oral | 5/5 |
|  | 5 |  | 5/5 |
|  | 2.5 |  | 4/5 |
|  | 1.25 |  | 2/5 |

TABLE 7

Antimalarial activity against *P. falciparum* and *P. vivax* in Aotus monkeys

| | | # Monkey Cured*/# Monkey Used | |
|---|---|---|---|
| Compound | Dose (mg/kg) | *P. vivax* | *P. falciparum* |
| 3e | 0.5 | 0/2 |  |
|  | 1 | 2/2 | 2/2 |
|  | 3 | 2/2 |  |
| 2b | 0.5 | 0/2 |  |
|  | 1 | 0/2 | 2/2 |
|  | 3 | 1/2 |  |

*Monkeys stayed parasitemia free for 100 days post treatment.

TABLE 8

Death rates and date after single treatment with 1, 2b, and 3e by intragastric administration in rats (n = 4)

| Groups & Doses (Formulation) | Deaths | 1 | 2 | 3 | 4 | 5 | 6 | 7 | 8 | 9 | 10 | 11 | 12 |
|---|---|---|---|---|---|---|---|---|---|---|---|---|---|
| 1% CMC suspension | 0/4 | | | | | | | | | | | | |
| 1 in 1% CMC suspension | | | | | | | | | | | | | |
| 25 mg/kg | 0/4 | | | | | | | | | | | | |
| 50 mg/kg | 0/4 | | | | | | | | | | | | |
| 100 mg/kg | 0/4 | | | | | | | | | | | | |
| 200 mg/kg | 1/4 | | | | | | | | 1 | | | | |
| 400 mg/kg | 3/4 | | | | | | 1 | 2 | | | | | |
| 2b in 1% CMC suspension | | | | | | | | | | | | | |
| 50 mg/kg | 0/4 | | | | | | | | | | | | |
| 100 mg/kg | 0/4 | | | | | | | | | | | | |
| 200 mg/kg | 0/4 | | | | | | | | | | | | |
| 400 mg/kg | 0/4 | | | | | | | | | | | | |
| 800 mg/kg | 1/4 | | | | | 1 | | | | | | | |
| 3e in 1% CMC suspension | | | | | | | | | | | | | |
| 50 mg/kg | 0/4 | | | | | | | | | | | | |
| 100 mg/kg | 0/4 | | | | | | | | | | | | |
| 200 mg/kg | 0/4 | | | | | | | | | | | | |
| 400 mg/kg | 0/4 | | | | | | | | | | | | |
| 800 mg/kg | 0/4 | | | | | | | | | | | | |

CMC = carboxymethyl cellulose
administration for three days (at day 6, 7, and 8 post-inoculation) treatments (n = 2–5).

(e). Toxicity Study in Aotus monkey:

Protocol:

Two malaria double cured Aotus weighing 1027-695 grams respectively received single dose of 3 mg/kg orally of the two compounds 2b and 3e. The monkeys were weighed and pre-bleed for CBC and Chemistry (ALT, BUN, Creatinine) determination, and again three, seven and 15 days post treatment. Signs of toxicity such as anorexia, vomiting, diarrhea or behavior changes were recorded.

Results:

No adverse effects regarding anorexia, vomiting, diarrhea or behavior changes were observed during a 28 day observation period. No significant changes in body weight were observed. CBC parameters remained within normal ranges. A steady decrease of the hepatic enzyme GPT from 75.3 to 17.7 Units and of BUN from 24.35 to <10.00 were observed in one monkey during the observation period. However, the monkey did not present any GI or renal abnormal symptom, although these parameters are indicative of decrease in hepatic function.

(f). Antimalarial Activity against *P. falciparum* in Aotus monkey:

Protocol: Six (6) malaria naive Aotus lemurinus lemurinus (weigh 787-978 grms) were divided into two groups of two Aotus each plus two controls (MN13177 male and MN 13153 male) and infected with $5 \times 10^6$ *P. falciparum* FVO malaria parasites with 1 ml of an appropriate dilution in RPMI media intravenously on the saphenous vein. When their parasitemia reached $5 \times 10^4$ parasites/ul, treatment was started. Giemsa-stained thick blood smears were prepared daily with a prick in the ear marginal vein and parasites enumerated by the Earle and Perez method. Group 1 Aotus received 3e at 1 mg/kg once a day×three days. Group 2 Aotus received 2b at 1 mg/kg once a day×three days. The monkeys were weight and pre-bled for CBC and Chemistry (ALT, BUN, Creatinine) determination, and on day 4 post-treatmetne (PT). Bleedings for Pk determinations were carried out on day 1 PT at time 0, 1 hr, 7:30 hr and 24 hr PT.

Results: Results for this experiment are shown on Tables 6. Group 1 (receiving 3e) animals cleared the parasitemias on day 3 post treatment (PT) and remained negative up to 100 days PT. In group 2 (receiving 2b), one animal cleared on day 3 PT and the other one on day 4 PT remaining negative up to 100 days PT. The results indicated that both 2b and 3e at 1 mg/kg×3 days cured 2/2 P. falciparum FVO infections in Aotus monkeys.

(g). Antimalarial Activity against P. vivax in Aotus monkey:

Protocol: Fourteen (14) P. falciparum cured Aotus l. lemurinus monkeys (male and female) (weight 700-925 grms) were infected intravenously with $5 \times 10^6$ parasites of the P. vivax AMRU-1 strain diluted in RPMI media obtained from a donor and divided into two larger groups of 6 monkeys each (Group I and Group II) (2 monkeys per dose level), that received 3e and 6 monkeys (2 monkeys per dose level) that received 2b daily at 0.5, 1.0 and 3 mg/kg/day for a total of 3 days. Two monkeys were left has untreated controls. Treatment started when parasitemia reached 5,000 parasites×cc/mm on day 6 PI. Daily food intake was documented. Daily Giemsa-stained thick blood smears were prepared from a prick in the marginal ear vein and parasites enumerated by the Earle and Perez method. The animals were weighed at weekly intervals. Blood samples for Pk determination were collected at the following time points as follows: Day 0: CBC and chemistry panel (ALT. Creatinine and BUN); Day 4: CBC and chemistry Panel. CBC and chemistry panels were done the day prior to first dose and 24 hours after last dose and at weekly intervals thereafter.

Results: As shown on Tables 6, in Group I, two monkeys that received 0.5 mg/kg of 3e suppressed the parasitemia but needed re-treatment on day 10 PT with the next highest dose because the development of parasitemia. The other monkeys received 1 and 3 mg/kg of 3e remained negative until day 100 PT. In Group II, all monkeys except for one that received 3 mg/kg of 2b failed treatment and were retreated on day 3 PT with 3e at either 0.25, 0.5 or 1 mg/kg for three days. In the monkeys that received re-treatment at 0.25 mg/kg, one cleared on day 4 PT but needed to be treated with Mefloquine on day 8 PT due to a low platelet count. The other animals that had not been cleared by day 6 PT were treated with Mefloquine. In conclusion, pyrroloquinazolinediamine derivative 3e cured 4/4 infections of P. vivax in Aotus at 1 and 3 mg/kg×three days. Compound 2b at 0.5 and 1 mg/kg×3 are not active and at higher dose of 3 mg/kg× three days cured one out of two monkeys. The preferred compound of the invention is derivative 3e which has been shown to be effective against P. vivax. P. vivax is known to be very drug resistant to antifolates.

(h). Presumptive Causal Prophylactic Test against P. cynomolgi in Rhesus monkey:

Protocol:

(1). Type of study: This study is causal prophylactic test. Six Rhesus monkeys weighing 3-4 kg were randomized to 2 control animals and 2 groups of 2 experimental animals each.

(2). Donor monkey: A donor monkey was inoculated intravenously with 1.3 mL freshly-thawed frozen infected red blood cell. When the monkey developed gametocytemia, mosquito feedings were conducted on days 13 and 14 after inoculation. The donor was treated with intramuscular chloroquine hydrochloride (CQ) 10 mg/kg, once a day after the second mosquito feeding and continued for 7 days.

(3). Inoculation: On day 0, each of the monkeys was inoculated intravenously with 1-ml inoculum of suspension containing $1.0 \times 10^6$ P. cynomolgi sporozoites harvested from Anopheles dirus mosquitoes' salivary glands previously fed on the donor monkey.

(4). Testing Compound Administration Schedule: All monkeys received treatment on days -1, 0 and 1. The control monkeys received dimethylsulfoxide (DMSO) and the experimental animals received testing compound orally.

Results: Control monkeys developed parasitemia on day 8 after sporozoites challenges. In the group treated with 1 mg/kg of 3e, one monkey developed parasitemia on day 8 and one on day 11. Both monkeys received 3 mg/kg of the same compounds developed parasitemia on day 15, a protection of 7 days as compared with the untreated control. Compound 2b showed better protection activity than 3e. In the group received 1 mg/kg of WR288830, the parasitemia developed on day 9 in one monkey and the other on day 15. In the group treated with 3 mg/kg of 2b, one monkey was protected for 8 days and the other was protected for 15 days before the parasitemia were detected.

Combination Therapy:

It is contemplated that the compounds of the present invention can be administered alone, in combination with other derivatives of the invention and/or in combination with another class of antimalarials, including but not limited to chloroquine, mefloquine, tafenoquine, and artamisinin. A combination therapy approach may be used to prevent drug resistance and to reduce dosage.

Generally accepted dosage:

Mice: 1-220 mg/kg sid×3 days

Monkeys: 1-16 mg/kg sid×3-7 days

Humans: 1-10 mg/kg sid×3-7 days

It is recommended that the compositions of the present invention be delivered orally. Suitable carriers for oral dosage include but are not limited to tablets, emulsion, suspension and transdermal patch.

The composition of the present invention can be made into a pharmaceutical formulation that is compatible with its intended route of administration. Examples of routes of administration include parenteral, e.g., intravenous, intradermal, subcutaneous, oral (e.g., inhalation), transdermal (topical), transmucosal, rectal administration and oral administration. Oral Administration is preferred. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from about 0% to about 60% of the total volume.

The pharmaceutical formulation may also be in the form of a solution of a salt form of the active ingredient in an appropriate aqueous vehicle such as water or isotonic saline or dextrose solution.

The pharmaceutical formulations of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical formulations may be formulated in a conventional manner using one or more physiologically acceptable carriers, which may be selected from excipients and auxiliaries that facilitate processing of the active compounds into preparations which can be used pharmaceutically.

For oral administration, the compounds of the present invention can be formulated readily by combining with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (compound), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum horoi, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds and agents.

Pharmaceutical formulations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the formulations may take the form of tablets or lozenges formulated in conventional manner.

Oral formulations generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral formulations can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds of the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

Aternatively, other delivery systems for hydrophobic pharmaceutical formulations may be employed. Liposomes and emulsions are known examples of delivery vehicles or carriers for hydrophobic drugs and cosmetics. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical formulations also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, and the like. Salts tend to be more soluble in aqueous or other protonic solvents than are the corresponding free-base forms.

In one embodiment, the compounds of the present invention are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically or cosmetically acceptable carriers. These can be prepared according to methods known to those skilled in the art, for example, as described in U.S. Pat. No. 4,522,811.

It is especially advantageous to formulate oral or parenteral formulations in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

In accordance with a convention used in the art, ⅹ is used in structural formulas and "—" as in, for example, "—CH₃" herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (n-Bu), isobutyl (i-Bu), t-butyl (t-Bu), (sec-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain. An "acyl" is intended to mean a —C(O)—$R^a$ radical, where $R^a$ is a suitable alkyl or aryl substituents.

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

References (Incorporated Herein by Reference. The Relevant Page Numbers Are Given.)

1. (a). Trigg, P. I., and A. V. Kondrachine (1998) The Current Global Malaria Situation, Chapter 2, p. 11-22, in MALARIA PARASITE BIOLOGY, PATHOGENESIS AND PROTECTION. Ed. I. W. Sherman, ASM Press, Washington, D.C., (b). World Health Organization.: World malaria situation in 1994. Wkly Epidemiol Rec. 1997; 72: 269-76., (c). Greenberg A. E., and Lobel H. O.: Mortality from *Plasmodium falciparum* malaria in travelers from the United States, 1959-1987. Ann Intern Med 1990; 113: 326-27.
2. White, N. J. (1998) Br. Med. Bull. 54:703-715.
3. Wallace M. R., Sharp T. W., Smoak B., et al.: Malaria among United States troops in Somalia. Am J Med 1996; 100: 49-55.
4. Nosten, F.; Ter Kuile, F.; Chongsuphajaisiddhi, T.; Luxemburger, C.; Webster, H. K.; Edstein, M.; Phaipun, L.; White, N. J. Mefloquine-resistant Falciparum Malaria on the Thai-Burmes Border, Lancet (1982), 337, 1140-1143.
5. Oduola, A. M.; Milhous, W. K.; Salako, L. A.; Walker, O.; Desjardins, R. E.; Reduced In Vitro Susceptibility to Mefloquine in West African Isolates of *Plasmodium falciparum*. Lancet (1987), 2, 1304-1305.
6. (a). Carson, P. E.; Flanagan, C. I., Ickes, C. E. and Alving, A. S. (1956), Enzymatic Deficiency in Primaquine-sensitive Erythrocytes, Science, (Washington), 124, 484-485., (b). Carson, P. E., Hohl, R., Nora, M. V., Parkhurst, G. W., Ahmad, T., Scanlan, S. and Frischer, H. (1981), Toxicology of the 8-Aminoquinolines and Generic Factors Associated with Their Toxicity in Man. Bulletin of the World Health Organization. 59, 427-437.
7. (a). Phillips-Howard PA and ter Kuile FO: CNS Adverse Events Associated with Antimalarial Agents: Fact or Fiction? Drug Safety (1995): 12:370-383., (b). Schlagenhauf, P. (1999). Mefloquine for malaria chemoprophylaxis 1991-1998. J Travel Med 6:122-123.
8. Ledig, Kurt W., 7-(Substituted)-7H-pyrrolo[3,2,-f] quinazoline-1,3-diamines, U.S. U.S. Pat. No. 4,118,561 (1978).
9. Thomas R. Sweeney (TRS) Malaria Compendium, WRAIR, Table 100, Page 817.
10. WRAIR unpublished data.
11. Desjardins, R. E.; Canfield, C. J.; Haynes, D. E.; Chulay, J. D. Quantitative Assessment of Antimalarial Activity In Vitro by a Semiautomated Microdilution Technique. *Antimicrob. Agents Chemother*. 1979, 16, 710-718.
12. Chulay, J. D.; Haynes, J. D.; Diggs, C. L. *Plasmodium falciparum*: Assessment of In Vitro Growth by [³H] hypoxanthine Incorporation. *Exp. Parasitol*. 1983, 55, 138-146.
13. Oduola, A. M.; Weatherly, N. F.; Bowdre, J. H.; Desjardins, R. E. *Plasmodium falciparum*: Cloning by Single-erythrocyte Micromanipulation and Heterogeneity In Vitro. *Exp. Parasitol*. 1988, 66, 86-95.

What is claimed is:

1. A compound of the formula I:

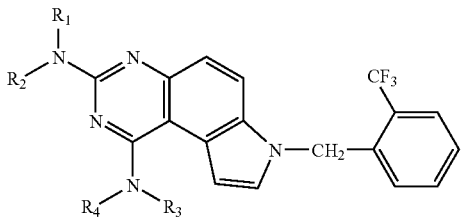

Formula I wherein R₁ is H, CH₃CH₂OC=O, (CH₃)₂CHOC=O, (CH₃)₃COC=O, or
(CH₃)₂CHCH₂OC=O R₂ is H, CH₃CH₂OC=O, (CH₃)₂CHOC=O, (CH₃)₃COC=O, or
(CH₃)₂CHCH₂OC=O R₃ is H, CH₃CH₂OC=O, (CH₃)₂CHOC=O, (CH₃)₃COC=O,
(CH₃)₂CHCH₂OC=O, or

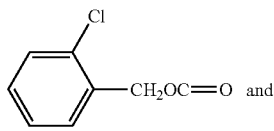

and

R₄ is H, CH₃CH₂OC=O, (CH₃)₃COC=O, (CH₃)₂CHCH₂OC=O, or

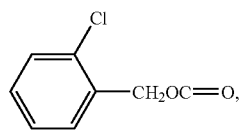

wherein R₁, R₂, R₃ and R₄ are not all simultaneously H.

2. The compound of claim 1, wherein: R₁ is H, R₂ is H, R₃ is CH₃CH₂OC=O and R₄ is H (2a).

3. The compound of claim 1, wherein R₁ is CH₃CH₂OC=O, R₂ is H, R₃ is H, and R₄ is H (2a').

4. The compound of claim 1, wherein R₁ is CH₃CH₂OC=O, R₂ is H, R₃ is CH₃CH₂OC=O, and R₄ is H (2b).

5. The compound of claim 1, wherein R₁ is CH₃CH₂OC=O, R₂ is H, R₃ and R₄ are CH₃CH₂OC=O (2c).

6. The compound of claim 1, wherein R₁, R₂, R₃ and R₄ are CH₃CH₂OC=O (2d).

7. The compound of claim 1, wherein R₁ is (CH₃)₂CHOC=O, R₂ is H, R₃ is (CH₃)₂CHOC=O, and R₄ is H (2e).

8. The compound of claim 1, wherein R₁ is H, R₂, R₃ and R₄ are (CH₃)₂CHOC=O (2f).

9. The compound of claim 1, wherein R₁, R₂ and R₄ are H, and R₃ is (CH₃)₃COC=O (2 g).

10. The compound of claim 1, wherein R₁ and R₂ are H, and R₃ and R₄ are (CH₃)₃COC=O (2 h).

11. The compound of claim 1, wherein R₁ is H, R₂, R₃ and R₄ are (CH₃)₃COC=O (2i).

12. The compound of claim 1, wherein R₁, R₂, R₃ and R₄ are (CH₃)₃COC=O (2j).

13. The compound of claim 1, wherein R₁, R₂, and R₄ are H, and R₃ is (CH₃)₂CHCH₂OC=O (2k).

14. The compound of claim 1, wherein R₁ and R₃ are (CH₃)₂CHCH₂OC=O and R₂ and R₄ are H (21).

15. The compound of claim 1, wherein R₁ and R₂ are H and R₃ and R₄ are

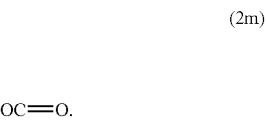

(2m)

16. A compound of the formula:

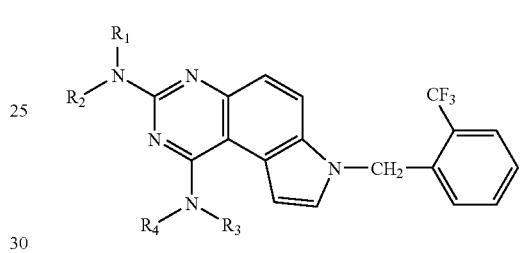

Formula 2 wherein R₁, R₂, R₃, and R₄ are independently a H, or CH₃C=O,or alkylacyl, arylacyl, or a pharmaceutically acceptable salt thereof and, wherein R₁, R₂, R₃ and R₄ are not all simultaneously H.

17. The compound of claim 16, wherein R₁, R₂ and R₄ are H, and R₃ is CH₃C=O (3a).

18. The compound of claim 16, wherein R₁ and R₂ are H and R₃ and R₄ are CH₃C=O (3b).

19. The compound of claim 16, wherein R₁ and R₃ are CH₃C=O and R₂ and R₄ are H (3c).

20. The compound of claim 16, wherein R₁ is H, R₂, R₃ and R₄ are CH₃C=O (3d).

21. The compound of claim 16 wherein R₁, R₂, R₃, R₄ are CH₃C=O (3e).

22. A compound of the formula 3:

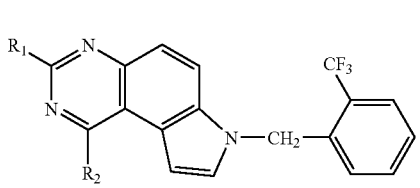

Formula 3

Wherein R₁, and R₂, are independently a NH₂,

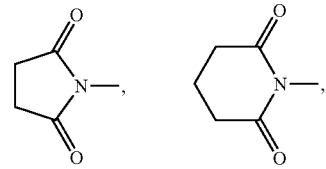

or

[structure: phthalimide-N-]

Where R₁ and R₂ are not all simultaneously NH₂.

23. The compound of claim 22, wherein R₁ is

[structure: succinimide-N-]

and R₂ is H (3 f).

24. The compound of claim 22, wherein R₁ and R₂ are (3g)

[structure: succinimide-N-]

25. The compound of claim 22, wherein R₁ is

[structure: glutarimide-N-]

and R₂ is H.

26. The compound of claim 22, wherein R₁ and R₂ are

[structure: glutarimide-N-]

27. The compound of claim 22, wherein R₁ is

[structure: phthalimide-N-]

and R₂ is H.

28. The compound of claim 22, wherein R₁ and R₂ are

[structure: phthalimide-N-]

29. A compound comprising formula 4:

formula 4

[structure of formula 4 with $H_2N$, OH, and $N-CH_2$-phenyl-R substituents]

Where R=$CF_3$, $CH_3$, $CH_3CH_2$, Cl, Br, or F.

30. A pharmaceutical composition comprising a compound of formula 5:

formula 5

[structure of formula 5 with $R_1$, $R_2$, $R_3$, $R_4$, $R_5$ substituents]

wherein $R_1$, $R_2$, $R_3$, and $R_4$ are independently H, $(CH_3)_2CH$, $(CH_3)_3C$, and $R_5$ is independently $CF_3$, $CH_3$, $CH_3CH_2$, Cl, Br, or F and, wherein $R_1$, $R_2$, $R_3$ and $R_4$ are not all simultaneously H.

31. An antimalaria composition comprising:
a pharmaceutically effective dosage unit of 1-220 mg/kg for treating malaria of the compound of claim 1.

32. An antimalaria composition comprising:
a pharmaceutically effective dosage unit of 1-220 mg/kg for treating malaria of the compound of claim 16.

33. An antimalaria composition comprising:
a pharmaceutically effective dosage unit of 1-220 mg/kg for treating malaria of the compound of claim 22.

34. An antimalaria composition comprising:
a pharmaceutically effective dosage unit of 1-220 mg/kg for treating malaria of the compound of claim 29.

35. A method of treating malaria in a patient in need thereof comprising: administering the compound of claim 1 at 1-16 mg/kg a day for 3-7 days or 1-220 mg/kg a day for 3 days.

36. A method of treating malaria in a patient in need thereof comprising: administering the compound of claim 16 at 1-16 mg/kg a day for 3-7 days or 1-220 mg/kg a day for 3 days.

37. A method of treating malaria in a patient in need thereof comprising: administering the compound of claim 29 at 1-16 mg/kg a day for 3-7 days or 1-220 mg/kg a day for 3 days.

38. A method of treating malaria in a patient in need thereof comprising: administering the compound of claim 30 at 1-16 mg/kg a day for 3-7 days or 1-220 mg/kg a day for 3 days.

39. The method of claim 35 further comprising administering one or more antimalarial composition selected from the group consisting of but not limited to chloroquine, mefloquine, tafenoquine, and artamisinin.

40. The method of claim 36 further comprising administering one or more antimalarial composition selected from the group consisting of but not limited to chloroquine, mefloquine, tafenoquine, and artamisinin.

41. The method of claim 37 further comprising administering one or more antimalarial composition selected from the group consisting of but not limited to chloroquine, mefloquine, tafenoquine, and artamisinin.

42. The method of claim 35 wherein said administering is done by oral route, transdermal, transmucosal, rectal, and intramuscular.

43. The method of claim 36 wherein said administering is done by oral route, transdermal, transmucosal, rectal, and intramuscular.

44. The method of claim 37 wherein said administering is done by oral route, transdermal, transmucosal, rectal, and intramuscular.

45. The method of claim 38 wherein said administering is done by oral route, transdermal, transmucosal, rectal, and intramuscular.

46. The method of claim 35, wherein said malaria is *P. falciparum* and/or *P. vivax*.

47. The method of claim 36, wherein said malaria is *P. falciparum* and/or *P. vivax*.

48. The method of claim 37, wherein said malaria is *P. falciparum* and/or *P. vivax*.

49. The method of claim 38, wherein said malaria is *P. falciparum* and/or *P. vivax*.

50. A pharmaceutical composition comprising a compound of the formula 6:

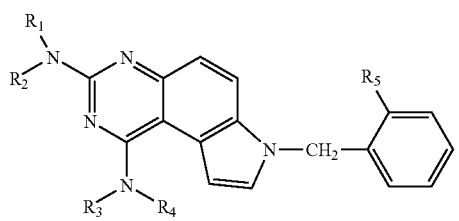

Formula 6

Where $R_1$, $R_2$, $R_3$, and $R_4$ are independently H, $CH_3C=O$, $(CH_2C=O)_2$, $CH_3CH_2C=O$, $(CH_3)_2CHC=O$, $(CH_3)_3CC=O$, or alkyl$C=O$,
$R_5$ is independently F, Cl, Br, $CH_3$, or $CH_3CH_2$
and, wherein $R_1$, $R_2$, $R_3$ and $R_4$ are not all simultaneously H.

51. A compound of the formula 7:

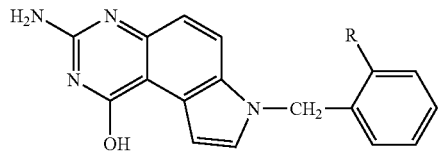

Formula 7

R=F, Cl, Br, $CH_3$, $CF_3$, or $CH_3CH_2$.

52. A method of preparation of a first and second (2b and 2c) compound of claim 1, comprising:
 a). mixing 7-[(2-trifluoromethyl-phenyl)methyl]-7H-pyrrolo[3,2-f]-quinazoline-1,3-diamine with triethylamine (1), and DMAP;
 b). adding ethyl chloroformate at 0° C.;
 c). bringing to room temperature and stirring;
 d). filtering with Celite to form a filtrate;
 e). washing the filtrate with $H_2O$;
 f). concentrating the filtrate;
 g). eluting with 2% $CH_3OH/CHCl_3$ in a silica gel column to yield a first alkylcarbamate of the compound of claim 1 wherein $R_1$ is $CH_3CH_2OC=O$,
 $R_2$ is H, $R_3$ is $CH_3CH_2OC=O$ (2b) and $R_4$ is H and a second alkylcarbamate of the compound of claim 1 wherein $R_1$ is $CH_3CH_2OC=O$,
 $R_2$ is H, $R_3$ and $R_4$ are $CH_3CH_2OC=O$ (2c); and
 h). recrystallizing said first alkylcarbamate and said second alkylcarbamate to form first alkylcarbamate crystals and second alkylcarbamate crystals.

53. The method of claim 52 further comprising the steps of: (2a)
 suspending said first alkylcarbamate crystals(2b) in ethyl acetate to make
 a suspension;
 refluxing said suspension;
 evaporating until dry to obtain a residue;
 applying said residue on a TLC plate and developing with $CH_3OH/CHCl_3$
 to yield a third alkylcarbamate 2a; and
 recrystalizing to give the third alkylcarbamate 2a crystals.

54. The method of claim 52 further comprising the steps of: (2a')
 suspending said first alkylcarbamate 2b crystals in $CH_3OH$;
 adding HCl and refluxing;
 neutralizing with saturated $NaHCO_3$;
 extracting with $CHCl_3$ to form an organic layer,
 washing the organic layer with $H_2O$ and drying to form a residue; and
 applying the residue to a silica gel column and eluding with
 $CH_3OH/CHCl_3$ to yield a fourth alkylcarbamate 2a'.

55. A method of preparation of a compound of claim 1 (2e), comprising:
 a). mixing 7-[(2-trifluoromethyl-phenyl)methyl]-7H-pyrrolo[3,2-f]-quinazoline-1,3-diamine with triethylamine (1), and DMAP;
 b). adding isopropyl chloroformate at 0° C.;
 c). bringing to room temperature and stirring;
 d). filtering with Celite to form a filtrate;
 e). washing the filtrate with $H_2O$;
 f). concentrating the filtrate;

g). eluting with 2% $CH_3OH/CHCl_3$ in a silica gel column to yield a fifth alkylcarbamate of the compound of claim 1 wherein $R_1$ is $(CH_3)_2CHOC=O$, $R_2$ is H, $R_3$ is $(CH_3)_2CHOC=O$, and $R_4$ is H (2e); and h). recrystallizing said fifth alkylcarbamate to form fifth alkylcarbamate crystals.

56. A method of preparation of a compound of claim 1 (2f), comprising:
a). mixing 7-[(2-trifluoromethyl-phenyl)methyl]-7H-pyrrolo[3,2-f]-quinazoline-1,3-diamine with triethylamine, and DMAP;
b). adding isopropyl chloroformate at 0° C.;
c). bringing to room temperature and stirring;
d). filtering with Celite to form a filtrate;
e). washing the filtrate with $H_2O$;
f). concentrating the filtrate;
g). eluting with 2% $CH_3OH/CHCl_3$ in a silica gel column to yield a sixth alkylcarbamate of the compound of claim 1 wherein $R_1$ is H, $R_2$, $R_3$ and $R_4$ are $(CH_3)_2CHOC=O$ (2f); and
h). recrystallizing said sixth alkylcarbamate to form sixth alkylcarbamate crystals.

57. A method of preparation of a compound of claim 1 (2j), comprising:
a). mixing 7-[(2-trifluoromethyl-phenyl)methyl]-7H-pyrrolo[3,2-f]-quinazoline-1,3-diamine with triethylamine, and DMAP;
b). adding t-butyl bicarbonate at 0° C.;
c). bringing to room temperature and stirring;
d). filtering with Celite to form a filtrate;
e). washing the filtrate with $H_2O$;
f). concentrating the filtrate;
g). eluting with 2% $CH_3OH/CHCl_3$ in a silica gel column to yield a seventh alkylcarbamate of the compound of claim 1 wherein $R_1$, $R_2$, $R_3$ and $R_4$ are $(CH_3)_3COC=O$ (2j); and
h). recrystallizing said seventh alkylcarbamate to form seventh alkylcarbamate crystals.

58. A method of preparation of a compound of claim 1 (2l), comprising:
a). mixing 7-[(2-trifluoromethyl-phenyl)methyl]-7H-pyrrolo[3,2-f]-quinazoline-1,3-diamine with triethylamine, and DMAP;
b). adding isobutyl chloroformate at 0° C.;
c). bringing to room temperature and stirring;
d). filtering with Celite to form a filtrate;
e). washing the filtrate with $H_2O$;
f). concentrating the filtrate;
g). eluting with 2% $CH_3OH/CHCl_3$ in a silica gel column to yield an eighth alkylcarbamate of the compound of claim 1 wherein $R_1$ and $R_3$ are $(CH_3)_2CHCH_2OC=O$ and $R_2$ and $R_4$ are H (2l); and
h). recrystallizing said eighth alkylcarbamate to form eighth alkylcarbamate crystals.

59. A method of preparation of a compound of claim 1 (2m), comprising:
a). mixing 7-[(2-trifluoromethyl-phenyl)methyl]-7H-pyrrolo[3,2-f]-quinazoline-1,3-diamine with triethylamine, and DMAP;
b). adding 2-chlorobenzyl chloroformate at 0° C.;
c). bringing to room temperature and stirring;
d). filtering with Celite to form a filtrate;
e). washing the filtrate with $H_2O$;
f). concentrating the filtrate;

g). eluting with 2% $CH_3OH/CHCl_3$ in a silica gel column to yield a ninth alkylcarbamate of the compound of claim 1 wherein, $R_1$ and $R_2$ are H and $R_3$ and $R_4$ are

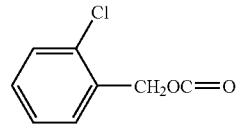

(2m); and h). recrystallizing said ninth alkylcarbamate to form ninth alkylcarbamate crystals.

60. A method of preparation of the compounds of claim 16, (3a-3e) comprising:
a). suspending 7-[2-trifluoromethyl-phenyl)methyl]-7H-pyrrolo[3,2-f]quinazoline-1,3-diamine (1) in anhydrous chloroform to form a suspension;
b). adding dimethylaminopyridine and triethylamine at room temperature to form a first mixture;
c). cooling said first mixture to about 5° C. with an ice-bath
d). adding acetic anhydride to said first mixture to form a second mixture;
e). stirring said second mixture at about 5° C. and then heating at 80° C. for 48 hours;
f). removing solvent from said second mixture and distilling excess acetic anhydride to form a solid;
g). purifying said solid with silica gel column chromatography using ethylacetate in chloroform to yield solid;
h). purifying said solid by recrystallization with EtOAc/Hexanes to yield crystals of
a first acetamide 3a wherein $R_1$, $R_2$ and $R_4$ are H, and $R_3$ is $CH_3C=O$,
a second acetamide 3b wherein $R_1$ and $R_2$ are H and $R_3$ and $R_4$ are $CH_3C=O$,
a third acetamide 3c wherein $R_1$ and $R_3$ are $CH_3C=O$ and $R_2$ and $R_4$ are H,
a forth acetamide 3d wherein $R_1$ is H, $R_2$, $R_3$ and $R_4$ are $CH_3C=O$, and a
fifth acetamide 3e wherein $R_1$, $R_2$, $R_3$, $R_4$ are $CH_3C=O$.

61. A method of preparation of a compound of claim 22, comprising:
a). suspending 7-[(2-trifluoromethyl-phenyl)methyl]-7H-pyrrolo[3,2-f]-quinazoline-1,3-diamine (1) in anhydrous p-xylene to form a suspension;
b). adding dry molecular sieves, DMAP and succinic anhydride to said suspension at room temperature and stirring;
c). adding triethylamine at room temperature;
d). refluxing;
e). cooling;
f). filtering to remove the molecular sieves;
g). evaporating until dry to form a solid residue;
h). purifying the solid residue first with a flush silica gel column using ethyl acetate in chloroform as eluent to provide an amorphous solid; and i). recrystallizing with CHCl$_3$/acetone to form crystals of a first succinimide (3 f) wherein R$_1$ is

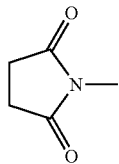

and R$_2$ is H and a second succinimide (3 g) wherein R$_1$ and R$_2$ are

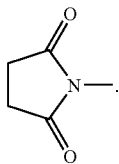

62. A method of preparing the compound of claim 29, comprising:
a). adding hydrochloric acid to a reaction mixture of 7-(2-trifluoromethyl)benzyl-7H-pyrrolo[3,2-f]-quinazoline-1,3-diamine in DMF at room temperature to make an aqueous solution; refluxing said aqueous solution;
b). chilling the aqueous solution and adjusting the pH of the solution to pH 7 with NaOH to form a tan color precipitate;
c). collecting the tan color precipitate and washing with water and drying in vacuo to form a crude product;
d). purifying the crude product by flush silica gel column chromatography using methanol in CHCl$_3$ as eluent to yield said compound of formula 4.

63. A method of preparing the compound of claim 30, comprising:
a). adding NaH in small portions at room temperature to a suspension of 7-(2-trifluoromethyl)benzyl-7H-pyrrolo[3,2-f]-quinazoline-1,3-diamine (1) in anhydrous THF to form a reaction mixture;
b). stirring the reaction mixture and then adding ethyl bromide to form a resulting reaction mixture;
c). stirring the resulting reaction mixture at room temperature;
d). quenching with H$_2$O to form a solution;
e). extracting the solution with ethyl acetate; and
f). drying and concentrating in vacuo to form a residue; and
g). yielding the compound of formula 5.

64. A method of treating malaria comprising:
administering a pharmaceutically effective amount of the compound of claim 22.

65. The method of claim 64, further comprising administering one or more antimalaria composition(s) selected from the group consisting of but not limited to chloroquine, mefloquine, tafenoquine, and artamisinin.

66. The method of claim 38, further comprising administering one or more antimalaria composition(s) selected from the group consisting of but not limited to chloroquine, mefloquine, tafenoquine, and artamisinin.

* * * * *